(12) United States Patent
Rosen et al.

(10) Patent No.: US 11,396,520 B2
(45) Date of Patent: *Jul. 26, 2022

(54) SYNTHESIS OF THE ORGANOARSENICAL ANTIBIOTIC ARSINOTHRICIN AND DERIVATIVES THEREOF

(71) Applicants: Barry P. Rosen, Boynton Beach, FL (US); Stanislaw F. Wnuk, Miami, FL (US); Masafumi Yoshinaga, Doral, FL (US); Md Abu Hasan Howlader, Miami, FL (US); Sk Md Sazzad Hossain Suzol, Philadelphia, PA (US)

(72) Inventors: Barry P. Rosen, Boynton Beach, FL (US); Stanislaw F. Wnuk, Miami, FL (US); Masafumi Yoshinaga, Doral, FL (US); Md Abu Hasan Howlader, Miami, FL (US); Sk Md Sazzad Hossain Suzol, Philadelphia, PA (US)

(73) Assignee: THE FLORIDA INTERNATIONAL UNIVERSITY BOARD OF TRUSTEES, Miami, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/186,538

(22) Filed: Feb. 26, 2021

(65) Prior Publication Data
US 2021/0380615 A1 Dec. 9, 2021

Related U.S. Application Data

(63) Continuation of application No. 16/893,890, filed on Jun. 5, 2020, now Pat. No. 10,934,318.

(51) Int. Cl.
*C07F 9/72* (2006.01)
*C12P 13/00* (2006.01)
(Continued)

(52) U.S. Cl.
CPC .............. *C07F 9/72* (2013.01); *A61B 17/083* (2013.01); *A61B 17/10* (2013.01); *C12P 13/001* (2013.01); *A61B 17/29* (2013.01)

(58) Field of Classification Search
CPC .................................. C07F 9/72; C12P 13/001
See application file for complete search history.

(56) References Cited

U.S. PATENT DOCUMENTS 10,934,318 B1 * 3/2021 Rosen ............ C12Y 201/01137

OTHER PUBLICATIONS

Adams, S., et al., "The Arsonomethyl Analogue of 3-Phosphoglycerate." Biochemical Journal, 1983, 213: 211-215.
(Continued)

*Primary Examiner* — Deborah D Carr
(74) *Attorney, Agent, or Firm* — Saliwanchik, Lloyd & Eisenschenk

(57) ABSTRACT

The subject invention provides methods and procedures for synthesis and/or semi-synthesis of the novel antibiotic arsinothricin (AST) and derivatives. Arsinothricin (AST), a new broad-spectrum organoarsenical antibiotic, is a non-proteinogenic analog of glutamate that effectively inhibits glutamine synthetase. The subject invention provides chemical synthesis of an intermediate in the pathway of AST synthesis, hydroxyarsinothricin (AST-OH), which can be converted to AST by enzymatic methylation catalyzed by the ArsM As(III) S-adenosylmethionine methyltransferase. The methods provide a source of the novel antibiotic that will be required for future clinical trials. The subject invention also provides AST derivatives as a new class of antibiotics.

20 Claims, 16 Drawing Sheets

AST

AST-OH

(51) Int. Cl.
  *A61B 17/10*  (2006.01)
  *A61B 17/08*  (2006.01)
  *A61B 17/29*  (2006.01)

(56) References Cited

OTHER PUBLICATIONS

Kuramara, M., et al., "Arsinothricin, a Novel Organoarsenic Species Produced by a Rice Rhizosphere Bacterium." Environmental Chemistry, 2016, 13: 723-731.

Lavis, L.D., et al., "Synthesis and Utility of Fluorogenic Acetoxymethyl Ethers." Chemical Science, 2011, 2(3) 521-530.

Marapakala, K., et al., "A Disulfide-Bond Cascade Mechanism for Arsenic(III) S-Adenosylmethionine Methyltransferase." Acta Crystallographica Section D: Biological Crystallography, 2015, 71: 505-515.

Mowbray, S., et al., "Inhibition of Glutamine Synthetase: A Potential Drug Target in *Mycobacterium tuberculosis*." Molecules, 2014, 19:13161-13176.

Nadar, V.S., et al., "Arsinothricin, An Arsenic-Containing Non-Proteinogenic Amino Acid Analog of Glutamate, is a Broad-Spectrum Antibiotic." Communications Biology, 2019, 2(131): 1-12.

Qin, J., et al., "Biotransformation of Arsenic by a Yellowstone Thermoacidophilic Eukaryotic Alga." Proceedings of the National Academy of Sciences, 2009, 106(13): 5213-5217.

\* cited by examiner

SYNTHESIS OF THE ORGANOARSENICAL ANTIBIOTIC ARSINOTHRICIN AND DERIVATIVES THEREOF

CROSS-REFERENCE TO A RELATED APPLICATION

This application is a continuation application of U.S. Ser. No. 16/893,890, filed Jun. 5, 2020, which is incorporated herein by reference in its entirety.

GOVERNMENT SUPPORT

This invention was made with government support under Grant No. GM055425 awarded by National Institutes of Health. The government has certain rights in the invention.

BACKGROUND OF THE INVENTION

New antibiotics are urgently needed because the emergence of resistance has rendered many clinically used antibiotics ineffective. Human tuberculosis (TB), the top global infectious disease killer caused by *Mycobacterium tuberculosis* (MTB), is becoming more difficult to treat due to the drug resistance. The World Health Organization (WHO) declared multidrug-resistant (MDR) TB a global public health crisis, calling a pressing need for development of new and innovative antibiotics. In addition to MTB, the WHO recently issued a global priority pathogen list of antibiotic resistant bacteria that pose the greatest threat to human health to guide and promote research and development of new antibiotics (see world-wide-website: who.int/en/newsroom/detail/27-02-2017-who-publishes-list-of-bacteria-for-which-new-antibiotics-are-urgently-needed). The antibiotic-resistant bacteria include the six nosocomial pathogens whose first initials form the acronym ESKAPE (*Enterococcus faecium, Staphylococcus aureus, Klebsiella pneumoniae, Acinetobacter baumannii, Pseudomonas aeruginosa,* and *Enterobacter* spp.) pathogens.

Arsenic is the most ubiquitous environmental toxic substance and carcinogen, ranking first on the 2019 Environmental Protection Agency's (EPA's) and Agency for Toxic Substances and Disease Registry's (ATSDR's) Comprehensive Environmental Response, Compensation, and Liability Act (CERCLA) Substance Priority List <http://www.atsdr.cdc.gov/spl/>. Most organisms merely try to survive life in arsenic. In contrast, some members of microbial communities have found ways to use arsenic as weapons against other bacteria in the continual battle for dominance in microbial warfare.

The use of arsenicals as antimicrobial and anticancer agents is well-established. The first synthetic antimicrobial agents were the organoarsenicals atoxyl (p-aminophenylarsenate, also known as p-arsanilic acid) and salvarsan (arsphenamine). While salvarsan is no longer in clinical use, the organoarsenical melarsoprol, developed in 1949, is still recommended by the WHO for treatment of second-stage *Trypanosoma brucei* sleeping sickness. The aromatic arsenicals atoxyl, roxarsone (4-hydroxy-3-nitrophenylarsenate) and nitarsone (4-nitrophenylarsenate) are used world-wide as antimicrobials for the prevention of *Coccidia* and *Histomonas* infections in poultry. Arsenic trioxide is currently the treatment of choice for all-trans retinoic acid unresponsive acute promyelocytic leukemia.

Arsinothricin [2-amino-4-(hydroxymethylarsinoyl)-butanoic acid or AST] has broad-spectrum antibiotic activity and is effective against both Gram-positive and Gram-negative bacteria, including the World Health Organization ESKAPE pathogen carbapenem-resistant *Enterobacter cloacae* (CRE) and *Mycobacterium bovis* BCG, a causative agent of animal tuberculosis that is closely related to the human pathogen MTB. AST is a nonproteinogenic amino acid analog of glutamate that inhibits glutamine synthetase, a crucial enzyme in formation of nitrogen compounds, presumably by mimicking the γ-acylphosphoglutamate intermediate in the glutamine synthetase reaction.

It is known that AST is produced by the rice rhizosphere bacterium *Burkholderia gladioli* GSRB05. However, the amounts of AST produced by such bacterium are insufficient for further biochemical and clinical characterization of this antibiotic. Overcoming this obstacle requires a chemical synthetic process. Thus, there is a need to develop novel methods for synthesizing AST and derivatives, ultimately, at a large scale, for animal testing, clinical trials and further drug development.

BRIEF SUMMARY OF THE INVENTION

The subject invention provides methods and procedures for synthesis and/or semi-synthesis of the antibiotic AST and derivatives. In one embodiment, the procedure combines chemical synthesis of the AST precursor or prodrug, 2-amino-4-(dihydroxyarsinoyl)butanoate), also known as hydroxyarsinothricin or AST-OH, with methylation by the thermostable enzyme CmArsM, an As(III)S-adenosylmethionine methyltransferase from the acidothermophilic eukaryotic algal strain *Cyanidioschyzon* sp. 5508 closely related to *Cyanidioschyzon merolae*.

The chemical synthesis and enzymatic methylation can be scaled up for the production of AST in amounts sufficient for further drug development. The subject invention provides methods for synthesizing AST-OH.

In one embodiment, the method for synthesizing AST according to the subject invention comprises steps for synthesizing AST-OH and steps of converting AST-OH to AST through an enzymatic methylation of AST-OH. In a preferred embodiment, the steps for synthesizing AST-OH comprise:

1) mixing halogen and/or OH-substituted alkane with an arsenous acid or a salt of an arsenous acid in the presence of a base to form a pentavalent arsenic acid;
2) optionally, adding a reducing agent, a catalytic agent and an acid to form a trivalent arsine;
3) optionally, adding an oxidizer to increase the oxidation state of As from III to V to form a second pentavalent arsenic acid;
4) adding a malonate compound and a base to form an aminated and carboxylated arsenic (V) acid;
5) adding second acid; and
6) optionally, purifying the product of step 5).

In a specific embodiment, the halogen and/or OH-substituted alkane includes, for example, haloalkane, such as 2-bromoethanol, 1,2-dibromoethane, 1-bromo-2-chloroethane, 2-chloroethanol and 1,2-dichloroethane. The salt of arsenous acid is, for example, $As(ONa)_3$. The reducing agent is, for example, $SO_2$. The catalytic agent is, for example, KI. The first and second acid may be the same or different. Preferably, the first and second acid are HCl. The oxidizer is, for example, $H_2O_2$. The malonate compound is, for example, diethyl acetamidomalonate. The base is, for example, a mixture of Na and EtOH.

In one embodiment, the steps for synthesizing AST-OH consist of:

mixing 2-chloroethanol with an arsenous acid or a salt of arsenous acid in the presence of a base to form a pentavalent arsenic acid;

adding a reducing agent, a catalytic agent and an acid to form a trivalent arsine, and subsequently, mixing with a halogen donor;

adding an oxidizer to form (2-chloroethyl)arsonic acid;

adding diethyl acetamidomalonate and sodium ethoxide to form $(EtO_2C—)_2C(—NH—Ac)—(CH_2)_2—AsO_3H_2$; and adding second acid to form AST-OH.

In one embodiment, the steps for synthesizing AST-OH comprise:

mixing 1,2-dichloroethane with an arsenous acid or a salt of arsenous acid in the presence of a base to form (2-chloroethyl)arsonic acid;

adding diethyl acetamidomalonate and sodium ethoxide to form $(EtO_2C—)_2C(—NH—Ac)—(CH_2)_2—AsO_3H_2$; and adding acid to form AST-OH.

In one embodiment, converting AST-OH to AST comprises mixing AST-OH with a reducing agent, e.g., an acidic mixture of $Na_2S_2O_3$, $Na_2S_2O_5$ and $H_2SO_4$, to reduce the oxidation state of As from (V) to (III); mixing the reduced mixture with NaOH, to neutralize the pH; and incubating the pH-neutralized mixture with an arsenite methyltransferase, e.g., As(III)S— adenosylmethionine (SAM) methyltransferase.

The subject invention also provides derivatives of AST and/or AST-OH as progenitors of antibiotics. The derivatives of AST and/or AST-OH according to the subject invention have the ability to inhibit GS. In preferred embodiments, the derivatives of AST and/or AST-OH have improved biological activity, increase permeability and uptake, and/or evade bacterial arsinothricin resistance mechanisms such as arsinothricin N-acetyltransferase or the homolog phosphinothricin N-acetyltransferase.

In certain embodiments, the derivatives of AST and/or AST-OH include pentavalent derivatives and trivalent derivatives. The derivative of AST and/or AST-OH has a general structure of formula

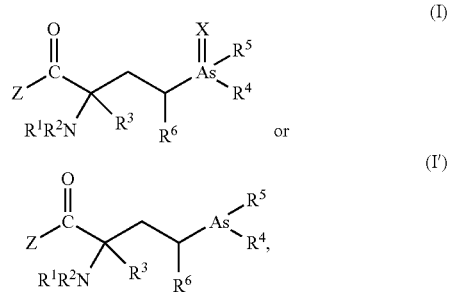

wherein X is O or S; Z is $OR^7$, $NHR^8$, $NR^8R^9$ or $NHCHR^{10}OR^{11}$; $R^1$, $R^2$, $R^3$, $R^4$, $R^5$, $R^6$, $R^7$, $R^8$, $R^9$, $R^{10}$, and $R^{11}$ are independently selected from, for example, hydrogen, alkyl, substituted alkyl, aryl, substituted aryl, benzyl, substituted benzyl, benzoyl, substituted benzoyl, heteroalkyl, substituted heteroalkyl, heteroaryl, substituted heteroaryl, cycloalkyl, substituted cycloalkyl, heterocycloalkyl, substituted heterocycloalkyl, cycloalkenyl, substituted cycloalkenyl, alkenyl, substituted alkenyl, alkynyl, alkoxy, substituted alkoxy, acyl, sulfhydryl, halogen, amino, substituted amino, hydroxyl, hydroxylalkyl, substituted hydroxylalkyl, $—C(O)R^{12}$, $—COOR^{13}$, and $—OR^{14}$, wherein $R^{12}$, $R^{13}$ and $R^{14}$ are independently selected from, for example, hydrogen, alkyl, substituted alkyl, aryl, substituted aryl, benzyl, substituted benzyl, benzoyl, substituted benzoyl, heteroalkyl, substituted heteroalkyl, heteroaryl, substituted heteroaryl, cycloalkyl, substituted cycloalkyl, heterocycloalkyl, substituted heterocycloalkyl, cycloalkenyl, substituted cycloalkenyl, alkenyl, substituted alkenyl, alkynyl, alkoxy, substituted alkoxy, acyl, sulfhydryl, halogen, amino, substituted amino, hydroxyl, hydroxylalkyl, and substituted hydroxylalkyl.

In a further embodiment, X is O or S; Z is $OR^7$ or $NHCHR^{10}R^{11}$; $R^1$ and $R^2$ are independently selected from hydrogen, alkyl, substituted alkyl, aryl, substituted aryl, acetyl, benzyl, and benzoyl; $R^3$ is hydrogen or alkyl; $R^4$ is OH, alkyl, substituted alkyl, aryl, substituted aryl, heteroalkyl, substituted heteroalkyl, acetyl, benzyl, benzoyl or sulfhydryl; $R^5$ is alkyl, substituted alkyl, aryl, substituted aryl, heteroalkyl, substituted heteroalkyl, acetyl, benzyl, benzoyl or sulfhydryl; Ra is hydrogen, or alkyl; $R^7$ is hydrogen, alkyl, substituted alkyl, aryl, substituted aryl, benzyl, benzoyl, heteroalkyl, or substituted heteroalkyl; $R^{10}$ is hydrogen, alkyl, or substituted alkyl; and $R^{11}$ is hydrogen, alkyl, substituted alkyl, aryl, substituted aryl, heteroalkyl, substituted heteroalkyl, alkoxy, amino, or substituted amino.

In specific embodiments, the derivative of AST and/or AST-OH has a structure of formula

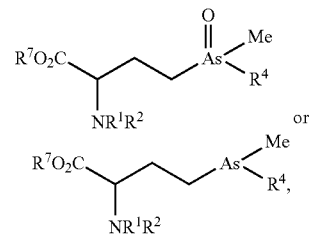

wherein $R^1$ and $R^2$ are independently selected from hydrogen, alkyl, substituted alkyl, benzoyl and benzyl, aryl, substituted aryl; $R^4$ is alkyl, substituted alkyl, aryl, substituted aryl, or sulfhydryl; and $R^7$ is hydrogen, alkyl, substituted alkyl, aryl, or substituted aryl. In a further embodiment, $R^1$ and $R^2$ are independently selected from methyl, acetyl, $CF_3CO$, benzoyl and benzyl; $R^4$ is methyl, phenyl, sulfhydryl or thiomethyl; and $R^7$ is H, methyl, ethyl, propyl, isopropyl, phenyl, or acetoxymethyl.

In further embodiments, the derivative of AST and/or AST-OH has a structure of formula

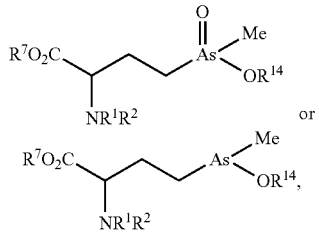

wherein $R^1$ and $R^2$ are independently selected from hydrogen, alkyl, substituted alkyl, aryl, and substituted aryl; $R^7$ is hydrogen, alkyl, substituted alkyl, aryl, or substituted aryl; and $R^{14}$ is alkyl, substituted alkyl, aryl, or substituted aryl. In a further embodiment, $R^1$ and $R^2$ are independently selected from methyl, acetyl, $CF_3CO$, benzoyl and benzyl;

$R^7$ is H, methyl, ethyl, propyl, isopropyl, phenyl, or acetoxymethyl; and $R^{14}$ is H, methyl, ethyl, propyl, phenyl, or acetoxymethyl.

In one embodiment, the derivative of AST and/or AST-OH has a structure of formula

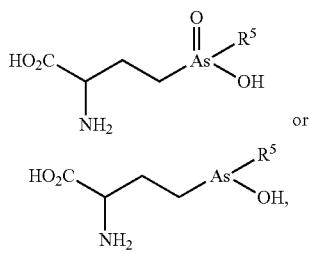

wherein $R^5$ is unsubstituted or substituted C2-C10 alkyl,

In one embodiment, the derivative of AST and/or AST-OH has a structure of formula

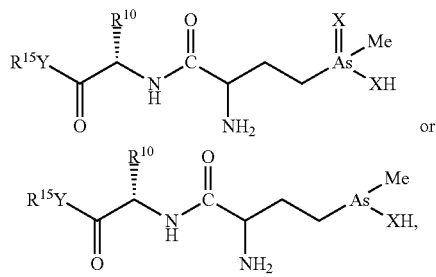

wherein X is O or S; Y is N or O; $R^{10}$ is alkyl, substituted alkyl, aryl, substituted aryl; and $R^{15}$ is alkyl, substituted alkyl, aryl, substituted aryl, or benzyl. In a further embodiment, Y is O; and $R^{15}$ is methyl, ethyl, propyl, isopropyl, acetoxymethyl, phenyl, $CH_2Ph$ or benzyl. In some embodiments, Y is N; and $R^{15}Y$ is an amino acid or a peptide comprising two, three, four, or five amino acids.

The subject invention further provides compositions comprising AST, AST-OH and/or a derivative or salt thereof, and a pharmaceutically acceptable carrier. Certain embodiments of the invention provide a method for treating an infection in a subject by using the composition comprising AST/AST-OH and/or a derivative or salt thereof. The infection may be caused by an infectious agent selected from, for example, a bacterium, a protozoan, a helminth, an archaebacterium, or a fungus.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DISCLOSURE OF THE INVENTION

Figure 1:
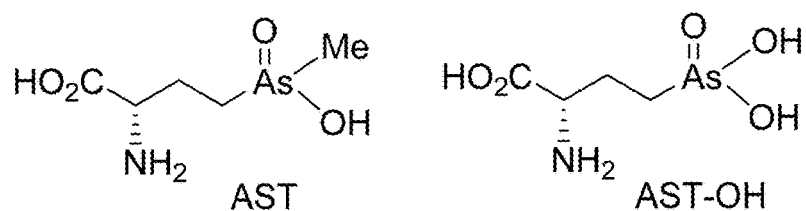
FIG. 1 shows the structures of arsinothricin (AST) and hydroxyarsi-nothricin (AST-OH).

The subject invention provides robust methods and procedures for synthesis and/or semi-synthesis of the antibiotic AST and derivatives. In preferred embodiments, The method combines chemical synthesis of the AST precursor or prodrug, 2-amino-4-(dihydroxyarsinoyl)butanoate, also known as hydroxyarsinothricin or AST-OH, with methylation by the thermostable enzyme As(III)S-adenosylmethionine methyltransferase (CmArsM) from the acidothermophilic eukaryotic alga *Cyanidioschyzon* sp. 5508 closely related to *C. merolae*. Advantageously, both the chemical synthesis and enzymatic methylation can be scaled up for the production of AST in amounts sufficient for further drug development.

The subject invention provides methods for synthesizing AST-OH. The methods according to the subject invention significantly improve the chemical synthesis of AST-OH, which, when coupled with AST-OH methylation by CmArsM completes the synthesis of AST. Advantageously, the synthesis methods of AST-OH are simple and involve fewer reaction steps.

AST is chemically unrelated to other organoarsenicals and can be modified to produce a new class of organoarsenical antibiotics. The subject invention also provides derivatives of AST and/or AST-OH as progenitors of antibiotics. Derivatives of AST and/or AST-OH AST are arsenic-containing compounds and may be produced by additional modifications of AST and/or AST-OH synthesized according to the subject invention. C—As (carbon-arsenic)-bond-containing compounds (arsonates) may be more effective as drugs than C—P (carbon-phosphorus)-bond-containing compounds (phosphonates), which include some of the most effective commercially available herbicides, pesticides and human drugs.

The subject invention further provides compositions comprising AST/AST-OH and/or derivatives and/or salts thereof, and methods for treating infections by using the composition comprising AST and/or derivatives and salts thereof. In some embodiments, the methods of treating infection in a subject utilize AST and/or derivatives and salts thereof, alone or in combination with an inhibitor of arsinothricin N-acetyltransferase or the homolog phosphinothricin N-acetyltransferase.

Certain embodiments of the subject invention provide methods of treating an infection in a subject caused by an infectious agent, the method comprising administering to the subject AST or AST-OH, and/or derivatives and/or salts thereof. AST and/or derivatives and salts thereof can be administered in the form of a pharmaceutical composition comprising pharmaceutically acceptable carriers.

Definitions

As used herein, the singular forms "a," "an," and "the" are intended to include the plural forms as well, unless the context clearly indicates otherwise. Furthermore, to the extent that the terms "including," "includes," "having," "has," "with," or variants thereof are used in either the detailed description and/or the claims, such terms are intended to be inclusive in a manner similar to the term "comprising." The transitional terms/phrases (and any grammatical variations thereof) "comprising," "comprises," and "comprise" can be used interchangeably; "consisting essentially of," and "consists essentially of" can be used interchangeably; and "consisting," and "consists" can be used interchangeably.

The transitional term "comprising," "comprises," or "comprise" is inclusive or open-ended and does not exclude additional, unrecited elements or method steps. By contrast, the transitional phrase "consisting of" excludes any element, step, or ingredient not specified in the claim. The phrases "consisting" or "consists essentially of" indicate that the claim encompasses embodiments containing the specified materials or steps and those that do not materially affect the basic and novel characteristic(s) of the claim. Use of the term "comprising" contemplates other embodiments that "consist" or "consisting essentially of" the recited component(s).

The term "about" or "approximately" means within an acceptable error range for the particular value as determined by one of ordinary skill in the art, which will depend in part on how the value is measured or determined, i.e., the limitations of the measurement system. For example, "about" can mean within 1 or more than 1 standard deviation, per the practice in the art. Alternatively, "about" can mean a range of up to 0-20%, 0 to 10%, 0 to 5%, or up to 1% of a given value. Where particular values are described in the application and claims, unless otherwise stated the term "about" meaning within an acceptable error range for the particular value should be assumed.

When ranges are used herein, such as for dose ranges, combinations and subcombinations of ranges (e.g., subranges within the disclosed range), specific embodiments therein are intended to be explicitly included.

The term "treatment" or any grammatical variation thereof (e.g., treat, treating, etc.), as used herein, includes but is not limited to, the application or administration to a subject (or application or administration to a cell or tissue from a subject) with the purpose of delaying, slowing, stabilizing, curing, healing, alleviating, relieving, altering, remedying, less worsening, ameliorating, improving, or affecting the disease or condition, the symptom of the disease or condition, or the risk of (or susceptibility to) the disease or condition. The term "treating" refers to any indication of success in the treatment or amelioration of a pathology or condition, including any objective or subjective parameter such as abatement; remission; lessening of the rate of worsening; lessening severity of the disease; stabilization, diminishing of symptoms or making the pathology or condition more tolerable to the subject; or improving a subject's physical or mental well-being.

The term "effective amount" or "therapeutically effective amount" refers to that amount of arsinothricin or a salt thereof, optionally, in combination with an inhibitor of phosphinothricin N-acetyltransferase or arsinothricin N-acetyltransferase, described herein that is sufficient to effect treatment of the infection. The therapeutically effective amount may vary depending upon the intended application, the subject, and the infection being treated, e.g., the weight and age of the subject, the severity of the infection, the manner of administration and the like, which can readily be determined by one of ordinary skill in the art. The specific dose will vary depending on the particular dosing regimen to be followed, whether it is administered in combination with other compounds, timing of administration, the tissue to which it is administered, and the physical delivery system in which it is carried.

The "salts" can be with an inorganic acid, such as hydrochloric acid, hydrobromic acid, perchloric acid, nitric acid, thiocyanic acid, sulfuric acid, and phosphoric acid; an organic acid, such as trifluoroacetic acid (TFA), formic acid, acetic acid, propionic acid, glycolic acid, lactic acid, pyruvic acid, oxalic acid, malonic acid, succinic acid, maleic acid, and fumaric acid; or a salt with a base, such as sodium hydroxide, ammonium hydroxide, potassium hydroxide, and organic bases such as mono-, di-, trialkyl and aryl amines, and substituted ethanolamines.

Further salts include: (1) acid addition salts, formed with inorganic acids such as sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl) benzoic acid, cinnamic acid, mandelic acid, methanesulfonic acid, ethanesulfonic acid, 1,2-ethane-di sulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo [2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or (2) salts formed when an acidic proton present in AST, derivatives, or salts thereof is either replaced by a metal ion, e.g., an alkali metal ion, an alkaline earth ion, a selenium ion or an aluminum ion; or coordinates with an organic base such as ethanolamine, diethanolamine, triethanolamine, N-methylglucamine and the like. Salts further include, by way of example only, sodium, potassium, calcium, magnesium, ammonium, tetraalkylammonium, and the like.

"Pharmaceutically acceptable carrier" or "pharmaceutically acceptable excipient" includes any and all solvents, dispersion media, coatings, antibacterial and antifungal agents, isotonic, and absorption delaying agents, and the like. The use of such media and agents for pharmaceutically active substances is well known in the art. Except insofar as any conventional media or agent is incompatible with the active ingredient, its use in the therapeutic compositions of the invention is contemplated. Supplementary active ingredients can also be incorporated into the compositions.

"Subject" refers to an animal, such as a mammal, for example a human. The methods described herein can be useful in both pre-clinical human therapeutics and veterinary applications. In some embodiments, the subject is a mammal (such as an animal model of disease), and in some embodiments, the subject is human. Non-limiting examples of subjects include canine, porcine, rodent, feline, bovine, poultry, equine, human, and a non-human primate.

As used herein, "alkyl" means linear saturated monovalent radicals of at least one carbon atom or a branched saturated monovalent of at least three carbon atoms. It may include hydrocarbon radicals of at least one carbon atom, which may be linear. It includes, for example, C1-C10 alkyl. Examples include, but not limited to, methyl, ethyl, propyl, 2-propyl, n-butyl, iso-butyl, tert-butyl, pentyl, hexyl, and the like.

As used herein, "acyl" means a radical —C(O)R where R includes, but is not limited to, hydrogen, alkyl, aryl, benzyl, benzoyl, heteroalkyl, heteroaryl, cycloalkyl, heterocycloalkyl, cycloalkenyl, alkenyl, alkynyl, alkoxy, sulfhydryl, halogen, amino, hydroxyl, hydroxylalkyl. Examples include, but are not limited to, formyl, acetyl, ethylcarbonyl, and the like. An aryl group may be substituted or unsubstituted.

As used herein, "alkylamino" means a radical —NHR or —NR$_2$ where each R is, independently, an alkyl or substituted alkyl group. Examples include, but are not limited to, methylamino, (1-methylethyl)amino, dimethyl amino, methylethylamino, di(1-methylethyl)amino, and the like. An alkylamino may be substituted or unsubstituted.

As used herein, "hydroxyalkyl" means an alkyl radical substituted with one or more hydroxy groups. Representative examples include, but are not limited to, hydroxymethyl, 2-hydroxyethyl; 2-hydroxypropyl; 3-hydroxypropyl; 1-(hydroxymethyl)-2-methylpropyl; 2-hydroxybutyl; 3-hydroxybutyl; 4-hydroxybutyl; 2,3-dihydroxypropyl; 2-hydroxy-1-hydroxymethylethyl; 2,3-dihydroxybutyl; 3,4-dihydroxybutyl and 2-(hydroxymethyl)-3-hydroxy-propyl, preferably 2-hydroxyethyl, 2,3-dihydroxypropyl and 1-(hydroxymethyl) 2-hydroxyethyl. A hydroxyalkyl may be substituted or unsubstituted.

As used herein, "alkenyl" refers to a straight or branched hydrocarbon chain containing one or more double bonds. The alkenyl group may have 2 to 9 carbon atoms, although the present definition also covers the occurrence of the term "alkenyl" where no numerical range is designated. The alkenyl group may also be a medium size alkenyl having 2 to 9 carbon atoms. The alkenyl group could also be a lower alkenyl having 2 to 4 carbon atoms. The alkenyl group may be designated as "C2-4 alkenyl" or similar designations. By way of example only, "C2-4 alkenyl" indicates that there are two to four carbon atoms in the alkenyl chain, i.e., the alkenyl chain is selected from ethenyl; propen-1-yl; propen-2-yl; propen-3-yl; buten-1-yl; buten-2-yl; buten-3-yl; buten-4-yl; 1-methyl-propen-1-yl; 2-methyl-propen-1-yl; 1-ethyl-ethen-1-yl; 2-methyl-propen-3-yl; buta-1,3-dienyl; buta-1,2,-dienyl and buta-1,2-dien-4-yl. Typical alkenyl groups include, but are in no way limited to, ethenyl, propenyl, butenyl, pentenyl, and hexenyl, and the like.

As used herein, "alkynyl" refers to a straight or branched hydrocarbon chain comprising one or more triple bonds. The alkynyl group may have 2 to 9 carbon atoms, although the present definition also covers the occurrence of the term "alkynyl" where no numerical range is designated. The alkynyl group may also be a medium size alkynyl having 2 to 9 carbon atoms. The alkynyl group could also be a lower alkynyl having 2 to 4 carbon atoms. The alkynyl group may be designated as "C2-4 alkynyl" or similar designations. By way of example only, "C2-4 alkynyl" indicates that there are two to four carbon atoms in the alkynyl chain, e.g., the alkynyl chain is selected from ethynyl, propyn-1-yl, propyn-2-yl, butyn-1-yl, butyn-3-yl, butyn-4-yl, and 2-butynyl. Typical alkynyl groups include, but are in no way limited to, ethynyl, propynyl, butynyl, pentynyl, and hexynyl, and the like.

As used herein, "cycloalkyl" means a fully saturated carbocyclyl ring or ring system. Examples include, but are not limited to, cyclopropyl, cyclobutyl, cyclopentyl, and cyclohexyl.

As used herein, "aryl" refers to a carbocyclic (all carbon) monocyclic or multicyclic aromatic ring system (including fused ring systems where two carbocyclic rings share a chemical bond). The number of carbon atoms in an aryl group can vary. For example, the aryl group can be a C6-C14 aryl group, a C6-C10 aryl group, or a C6 aryl group. Examples of aryl groups include, but are not limited to, phenyl, benzyl, α-naphthyl, β-naphthyl, biphenyl, anthryl, tetrahydronaphthyl, fluorenyl, indanyl, biphenylenyl, and acenaphthenyl. Preferred aryl groups are phenyl and naphthyl.

As used herein, "heteroaryl" refers to an aromatic ring or ring system (i.e., two or more fused rings that share two adjacent atoms) that comprise(s) one or more heteroatoms, that is, an element other than carbon, including but not limited to, nitrogen, oxygen and sulfur, in the ring backbone. When the heteroaryl is a ring system, every ring in the system is aromatic. The heteroaryl group may have 5-18 ring members (i.e., the number of atoms making up the ring backbone, including carbon atoms and heteroatoms), although the present definition also covers the occurrence of the term "heteroaryl" where no numerical range is designated. Examples of heteroaryl rings include, but are not limited to, furyl, thienyl, phthalazinyl, pyrrolyl, oxazolyl, thiazolyl, imidazolyl, pyrazolyl, isoxazolyl, isothiazolyl, triazolyl, thiadiazolyl, pyridinyl, pyridazinyl, pyrimidinyl, pyrazinyl, triazinyl, quinolinyl, isoquinlinyl, benzimidazolyl, benzoxazolyl, benzothiazolyl, indolyl, isoindolyl, and benzothienyl.

As used herein, "haloalkyl" refers to an alkyl group in which one or more of the hydrogen atoms is replaced by a halogen (e.g., mono-haloalkyl, di-haloalkyl and tri-haloalkyl). Such groups include but are not limited to, chloromethyl, fluoromethyl, difluoromethyl, trifluoromethyl and 1-chloro-2-fluoromethyl, 2-fluoroisobutyl. A haloalkyl may be substituted or unsubstituted.

As used herein, a "substituted" group may be substituted with one or more group(s) individually and independently selected from alkyl, alkenyl, alkynyl, cycloalkyl, cycloalkenyl, cycloalkynyl, benzyl, substituted benzyl, substituted benzoyl, benzoyl, acetyl, aryl, heteroaryl, heteroalicyclyl, aralkyl, heteroaralkyl, (heteroalicyclyl)alkyl, hydroxy, protected hydroxyl, alkoxy, aryloxy, acyl, carboxyl, COOR, CH$_2$COR, CH$_2$COOR, mercapto, alkylthio, arylthio, cyano, halogen, thiol, thiocarbonyl, O-carbamyl, N-carbamyl, O-thiocarbamyl, N-thiocarbamyl, C-amido, N-amido, S-sulfonamido, N-sulfonamido, C-carboxy, protected C-carboxy, O-carboxy, isocyanato, thiocyanato, isothiocyanato, nitro, silyl, sulfenyl, sulfinyl, sulfonyl, haloalkyl, haloalkoxy, trihalomethanesulfonyl, trihalomethanesulfonamido, an amino, a mono-substituted amino group and a di-substituted amino group, alkylamino, arylamino, amino acid(s) and protected derivatives thereof.

As used herein, "halogen" refers to an atom of fluorine, chlorine, bromine or iodine.

As used herein, "homocyclic ring" refers to cycloalkyl or aryl.

As used herein, "heterocyclic ring" refers to a ring, which may contain 1 to 4 heteroatoms selected from among nitrogen, oxygen, sulfur and other atoms in addition to carbon atoms.

Methods for Producing AST and Derivatives

Figure 2:
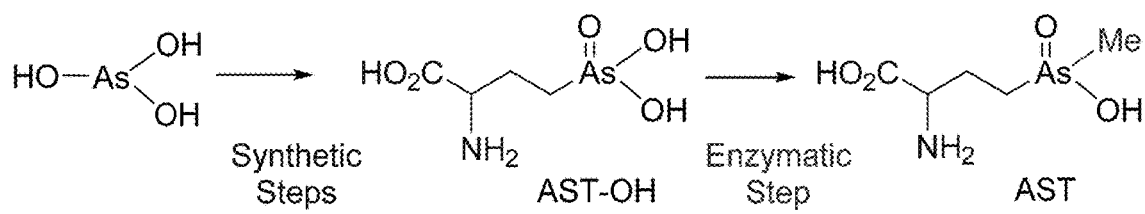
FIG. 2 shows the overall scheme for the production of AST.

The subject invention provides a synthesis or semi-synthetic procedure of AST (e.g., FIG. 1), involving chemical synthesis of the precursor or prodrug of AST, AST-OH (FIG. 1), which is then enzymatically methylated to AST using a thermostable enzyme, arsenite methyltransferase, e.g., CmArsM (FIG. 2).

In a preferred embodiment, the method for producing AST and/or derivatives according to the subject invention comprises steps for synthesizing AST-OH and a step of converting AST-OH to AST through an enzymatic methylation of AST-OH. In one embodiment, AST and/or AST-OH, or derivatives are synthesized from arsenous acid or salts of arsenous acid.

In one embodiment, the method for producing AST-OH comprises a plurality of chemical synthesis steps (e.g., FIG. 3), wherein the chemical synthesis comprises a) a step of alkylation of arsenous acid or salts of arsenous acid to form a pentavalent arsenic acid; b) a step to reduce the pentavalent arsenic acid to form a trivalent arsine compound; c) a step of oxidizing the trivalent arsine compound to form a second pentavalent arsenic acid; d) a step of alkylating the second pentavalent arsenic acid by coupling with a malonate compound comprising N-acyl protected primary or secondary amine; and e) a step of deprotection and decarboxylation to form AST-OH.

In one embodiment, the step a) of alkylation of arsenous acid or salts of arsenous acid to form a pentavalent arsenic acid comprises mixing an alkane or substituted alkane, e.g., haloalkane such as chloroalkane, and substituted haloalkane such as substituted chloroalkane, with arsenous acid or a salt of an arsenous acid in the presence of a base, wherein the alkylation of arsenous acid or the salt of arsenous acid occurs at arsenic (As), wherein the alkane is, preferably, an ethane, and wherein the alkane may be substituted by one or more halogen and/or —OH, e.g., substituted ethane. The pentavalent arsenic acid comprises one or more hydroxyl groups. Preferably, the pentavalent arsenic acid comprises a 2-hydroxyl.

In a further embodiment, the arsenous acid may result from the hydrolysis of arsenic trioxide. The base may be, e.g., NaOH, KOH, or CsOH. The salt of arsenous acid may be, e.g., a sodium, potassium, or cesium salt, preferably, a sodium salt, e.g., sodium arsenite. The substituted alkane may be, for example, 1,2-dibromoethane, 1-bromo-2-chloroethane, 1,2-dichloroethane, 2-chloroethanol, or 2-bromoethanol. In a specific embodiment, the step a) of alkylation of arsenous acid or salts of arsenous acid to form a pentavalent arsenic acid comprises mixing 2-chloroethanol with arsenic trioxide or $As(ONa)_3$ in the presence of NaOH, which produces a pentavalent arsenic acid, e.g., compound 2. The reaction can be performed at room temperature.

In one embodiment, the step b) of reducing the pentavalent arsenic acid to form a trivalent arsine compound comprises mixing the pentavalent arsenic acid with a reducing agent, wherein the mixture of the pentavalent arsenic acid and the reducing agent may further comprise a catalytic agent and an acid, preferably an excess amount of the acid. In a preferred embodiment, the reducing agent is $SO_2$, the catalytic agent is KI and the acid is HCl. The mixture has a pH value of 1-6.5, 1.5-6, 2-6, 2-5.5, 2-5, 2-4, 2-3, 2.5-5.5, 3-5.5, 3.5-5.5, 4-5.5, 4-5, or 4-6. The reaction can be performed at room temperature.

In a specific embodiment, the step b) of reducing the pentavalent arsenic acid to form a trivalent arsine compound comprises mixing compound 2 with KI, HCl and $SO_2$ to form a trivalent arsine compound, e.g., compound 3.

In a further embodiment, the step b) of reducing the pentavalent arsenic acid to form a trivalent arsine compound also comprises a step of substituting the hydroxyl group(s) of the trivalent arsine compound with a halogen, for example, by reacting with a halogen donor, e.g., thionyl chloride or thionyl bromide to form a chloro- or bromo-substituted trivalent arsine compound, e.g., compound 4.

In one embodiment, the step c) of oxidizing the trivalent arsine compound to form a second pentavalent arsenic acid comprises mixing the product of step b) with an oxidizer, e.g., $H_2O_2$ to form a second pentavalent arsenic acid, e.g., compound 5.

In one embodiment, the step d) of alkylating the second pentavalent arsenic acid by coupling with a malonate compound comprising N-acyl protected primary or secondary amine comprises mixing the second pentavalent arsenic acid with the malonate compound in the presence of a base, preferably, a strong base. Preferably, the malonate compound comprises N-acetyl protected primary or secondary amine. More preferably, the malonate compound is diethyl acetamidomalonate. The base is, e.g., sodium ethoxide, or a mixture of Na and EtOH.

This step may occur at an elevated temperature, for example, from about 40 to about 90° C., from about 50 to about 90° C., from about 50 to about 80° C., from about 60 to about 80° C., or from about 60 to about 70° C., preferably at about 50° C., 60° C., 70° C., 80° C., or 90° C. In a specific embodiment, the resulting compound of step d) is compound 7b.

In one embodiment, the step e) of deprotection and decarboxylation of the product of step d) comprises adding acid to the product of step d) to produce AST-OH. The acid can be selected from, e.g., HCl, $H_2SO_4$, and $HNO_3$. In a preferred embodiment, the acid has a concentration from 1 M to 20 M, 1 M to 15 M, 1 M to 10M, 2 M to 10 M, 2 M to 8 M, or 4 M to 8 M, more preferably, a concentration of 2 M, 3 M, 4 M, 5 M, 6 M, 7 M, 8 M, 9M, 10 M.

In one embodiment, the method for synthesizing AST-OH according to the subject invention does not comprise or require an esterification step, in particular, of compound 5.

The subject invention also provide a simplified synthesis method for producing AST-OH (FIG. 12), the method comprising chemical synthesis steps, wherein the chemical synthesis comprises i) a step of alkylation of arsenous acid or a salt of an arsenous acid to form a pentavalent arsenic acid; ii) a step of alkylating the pentavalent arsenic acid by coupling with a malonate compound comprising N-acyl protected primary or secondary amine; and iii) a step of deprotection and decarboxylation to form AST-OH.

In one embodiment, the step i) of alkylation of arsenous acid or a salt of an arsenous acid to form a pentavalent arsenic acid comprises mixing an alkane or substituted alkane, e.g., haloalkane such as chloroalkane, and substituted haloalkane such as substituted chloroalkane, with arsenous acid or a salt of an arsenous acid in the presence of a base, wherein the alkylation of arsenous acid or the salt of arsenous acid occurs at arsenic (As), wherein the alkane is, preferably, an ethane or substituted ethane, and wherein the alkane is substituted by one or more halogen and/or —OH. The pentavalent arsenic acid comprises one or more hydroxyl groups.

In a further embodiment, the arsenous acid may result from the hydrolysis of arsenic trioxide. The base may be, e.g., NaOH, KOH, or CsOH. The salt of arsenous acid may be, e.g., a sodium, potassium, or cesium salt, preferably, a sodium salt, e.g., sodium arsenite. The substituted alkane may be, for example, 1,2-chloroethane; 1,2-bromoethane; 1-chloro, 2-bromoethane; or 1-bromo, 2-chloroethane. In a specific embodiment, the step i) of alkylation of arsenous acid or salts of arsenous acid to form a pentavalent arsenic acid comprises mixing 1,2-chloroethane with arsenic trioxide in the presence of NaOH, which produces a pentavalent arsenic acid, e.g., compound 5. The reaction can be performed at room temperature.

In one embodiment, the step ii) of alkylating the pentavalent arsenic acid by coupling with a malonate compound comprising N-acyl protected primary or secondary amine comprises mixing the pentavalent arsenic acid with the malonate compound in the presence of a base, preferably, a strong base. Preferably, the malonate compound comprises N-acetyl protected primary or secondary amine. More preferably, the malonate compound is diethyl acetamidomalonate. The base may be, e.g., sodium ethoxide or a mixture of Na and EtOH. This step may occur at an elevated temperature, for example, from about 40 to about 90° C., from about 50 to about 90° C., from about 50 to about 80° C., from about 60 to about 80° C., or from about 60 to about 70° C., preferably, at about 50° C., 60° C., 70° C., 80° C., or 90° C. In a specific embodiment, the resulting compound of step ii) is compound 7b.

In one embodiment, the step iii) of deprotection and decarboxylation of the product of step d) comprises adding acid to the product of step d) to produce AST-OH. The acid can be selected from, e.g., HCl, $H_2SO_4$, and $HNO_3$. In a preferred embodiment, the acid has a concentration from 1 M to 20 M, 1 M to 15 M, 1 M to 10 M, 2 M to 10 M, 2 M to 8 M, or 4 M to 8 M, more preferably, a concentration of 2 M, 3 M, 4 M, 5 M, 6 M, 7 M, 8 M, 9M, 10 M.

Advantageously, the simplified synthesis method of AST-OH eliminates the necessity of conversion of the pentavalent arsenic acid, e.g., (2-hydroxyethyl)arsonic acid, to a trivalent arsine compound, e.g., dichloro(2-hydroxyethyl)arsine, with toxic $SO_2$ gas, and challenging displacement of hydroxyl group with chloride.

In one embodiment, the yield of each step in the synthesis method according to the subject invention is at least 5%, 10%, 15%, 20%, 25%, 30%, 35%, 40%, 45%, 50%, 55%, 60%, 65%, 70%, 75%, 80%, 85%, 90%, 95%, 98%, or 99%.

Figure 13:
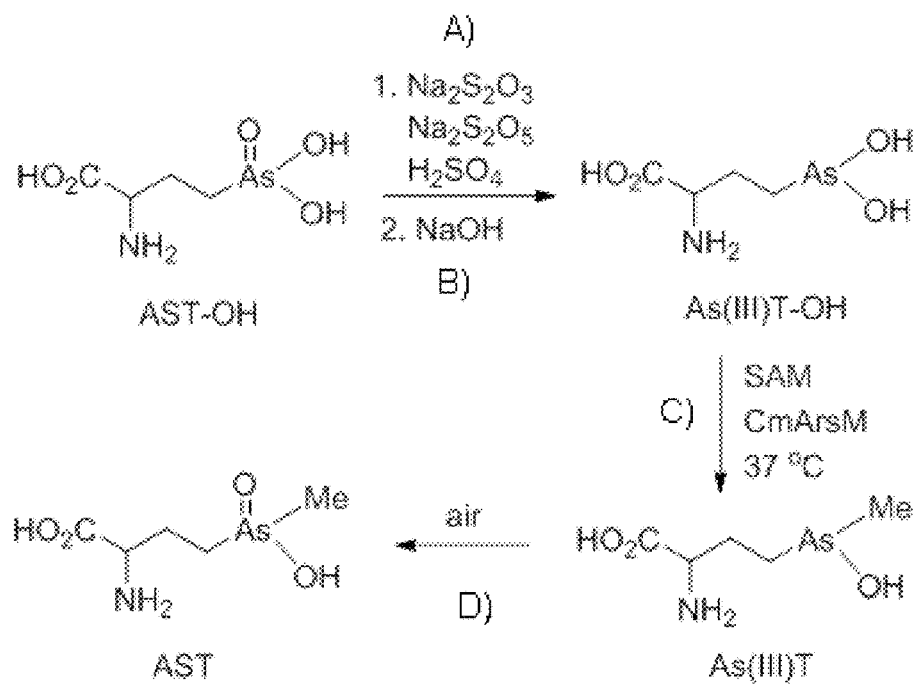
FIG. 13 shows enzymatic methylation of AST-OH to AST.

In one embodiment, the method for producing AST further comprises converting AST-OH to AST (FIG. 13). Such conversion process comprises A) reducing AST-OH to As(III)T-OH; B) neutralizing the pH of the reaction mixture with a base, e.g., NaOH; C) incubating As(III)T-OH with an arsenite methyltransferase (ArsM), e.g., As(III)S-adenosylmethionine (SAM) methyltransferase, preferably, ArsM from *Cyanidioschyzon* sp. 5508 (CmArsM); and optionally, D) letting the product of step C) set in the air for oxidization, wherein reducing AST-OH to As(III)T-OH comprises mixing AST-OH with a second reducing agent, preferably, the reducing agent comprises an acidic mixture of sodium thiosulfate and sodium disulfite and the acid is $H_2SO_4$. CmArsM catalyzes the transfer of the S-methyl group of SAM to As(III)T-OH, nearly completely converting it to the trivalent form of AST (As(III)T), as a mixture of the D/L-enantiomers, which is then oxidized in air to produce AST.

In one embodiment, the method for synthesizing/producing AST, according to the subject invention comprises or consists of:

1) mixing an alkane or substituted alkane with an arsenous acid or a salt of an arsenous acid in the presence of a base to form a pentavalent arsenic acid, and removing the precipitate;
2) adding a reducing agent, a catalytic agent and a first acid to form a trivalent arsine, extracting and drying the mixture, and subsequently, mixing with a halogen donor to substitute a hydroxyl group of the trivalent arsine with a halogen;
3) adding a solvent, e.g., water and an oxidizer to the product of step 2) and evaporating the solvent;
4) adding a malonate compound and a base to the product of step 3);
5) adding second acid to the product of step 4);
6) mixing the product of step 5) with a second reducing agent; and
7) incubating the product of step 6) with an arsenite methyltransferase (e.g., As(III)S-adenosylmethionine (SAM) methyltransferase);
wherein the first and second acid may be the same or different, and the first and second reducing agent may be the same or different.

In a specific embodiment, the method for synthesizing/producing AST comprises or consists of:

1) mixing 2-chloroethanol with $As_2O_3$ or $As(ONa)_3$ in the presence of NaOH and removing the precipitate;
2) adding $SO_2$, KI and HCl, extracting and drying the mixture;
3) adding chloroform and $SOCl_2$ to the dried mixture and evaporating chloroform;
4) adding water and $H_2O_2$ followed by evaporation;
5) adding diethyl acetamidomalonate, Na and EtOH to the product of step 4);
5) adding HCl;
6) mixing the product of step 5) with an acidic mixture of sodium thiosulfate and sodium disulfite; and
7) incubating the product of step 6) with an arsenite methyltransferase (e.g., As(III)S-adenosylmethionine (SAM) methyltransferase).

In one embodiment, the subject invention also provides a simplified method for synthesizing/producing AST that comprises or consists of:

1) mixing an alkane or substituted alkane with arsenous acid or a salt of an arsenous acid in the presence of a base and removing the precipitate;
2) adding a malonate product and a base;
3) adding an acid;
4) mixing the product of step 3) with a reducing agent; and
5) incubating the product of step 4) with an arsenite methyltransferase (e.g., As(III)S-adenosylmethionine (SAM) methyltransferase).

In a, specific embodiment, the simplified method for synthesizing/producing AST comprises or consists of:

1) mixing 1,2-dichloroethane with $As_2O_3$ or $As(ONa)_3$ in the presence of NaOH and removing the precipitate;
2) adding diethyl acetamidomalonate, Na and EtOH
3) adding HCl;
4) mixing the product of step 3) with an acidic mixture of $Na_2S_2O_3$ and $Na_2S_2O_5$; and
5) incubating the product of step 4) with an arsenite methyltransferase (e.g., As(III)S-adenosylmethionine (SAM) methyltransferase).

In one embodiment, the synthesized AST or AST-OH may be further modified with additional functional groups to produce AST derivatives having similar biological activity with AST.

In one embodiment, the method according to the subject invention further comprises purifying the product of each step prior to the next step and purifying AST or derivative after the final step.

AST Derivatives

The subject invention provides derivatives of AST and/or AST-OH. Such derivatives include pentavalent and/or trivalent derivatives of AST and/or AST-OH. Derivatives of AST and/or AST-OH are arsenic-containing compounds and may be produced by modification of AST and/or AST-OH synthesized according to the subject invention. In specific embodiments, the modification may be, for example, the introduction of an additional α- or γ-substituent, cyclization of the carbon backbone and/or modification of the methyl group.

The derivatives of AST and/or AST-OH according to the subject invention have the ability to inhibit GS. The derivatives of AST and/or AST-OH can have improved biological activity, increase permeability and uptake and/or evade bacterial arsinothricin resistance mechanisms such as arsinothricin N-acetyltransferase or the homolog phosphinothricin N-acetyltransferase.

In one embodiment, the derivatives of AST and/or AST-OH according to the subject invention include pentavalent derivatives and trivalent derivatives of AST.

In one embodiment, the pentavalent derivatives of AST or AST-OH have a general structure of formula (I):

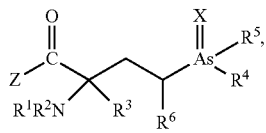

wherein X is O or S; Z is $OR^7$, $NHR^8$, $NR^8R^9$ or $NHCHR^{10}OR^{11}$; $R^1$, $R^2$, $R^3$, $R^4$, $R^5$, $R^6$, $R^7$, $R^8$, $R^9$, $R^{10}$, and $R^{11}$ are independently selected from, for example, hydrogen, alkyl, substituted alkyl, aryl, substituted aryl, benzyl, substituted benzyl, benzoyl, substituted benzoyl, heteroalkyl, substituted heteroalkyl, heteroaryl, substituted heteroaryl, cycloalkyl, substituted cycloalkyl, heterocycloalkyl, substituted heterocycloalkyl, cycloalkenyl, substituted cycloalkenyl, alkenyl, substituted alkenyl, alkynyl, alkoxy, substituted alkoxy, sulfhydryl, halogen, amino, substituted amino, hydroxyl, hydroxylalkyl, substituted hydroxylalkyl, —C(O)$R^{12}$, —COO$R^{13}$, nd O$R^{14}$, wherein $R^{12}$, $R^{13}$ and $R^{14}$ are independently selected from, for example, hydrogen, alkyl, substituted alkyl, aryl, substituted aryl, benzyl, substituted benzyl, benzoyl, substituted benzoyl, heteroalkyl, substituted heteroalkyl, heteroaryl, substituted heteroaryl, cycloalkyl, substituted cycloalkyl, heterocycloalkyl, substituted heterocycloalkyl, cycloalkenyl, substituted cycloalkenyl, alkenyl, substituted alkenyl, alkynyl, alkoxy, substituted alkoxy, acyl, sulfhydryl, halogen, amino, substituted amino, hydroxyl, hydroxylalkyl, and substituted hydroxylalkyl.

In one embodiment, the trivalent derivatives of AST or AST-OH have a general structure of formula (I'):

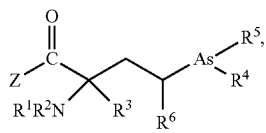

wherein X is O or S; Z is $OR^7$, $NHR^8$, or $NHCHR^{10}R^{11}$; $R^1$, $R^2$, $R^3$, $R^4$, $R^5$, $R^6$, $R^7$, $R^8$, $R^9$, $R^{10}$, and $R^{11}$ are independently selected from, for example, hydrogen, alkyl, substituted alkyl, aryl, substituted aryl, benzyl, substituted benzyl, benzoyl, substituted benzoyl, heteroalkyl, substituted heteroalkyl, heteroaryl, substituted heteroaryl, cycloalkyl, substituted cycloalkyl, heterocycloalkyl, substituted heterocycloalkyl, cycloalkenyl, substituted cycloalkenyl, alkenyl, substituted alkenyl, alkynyl, alkoxy, substituted alkoxy, sulfhydryl, halogen, amino, substituted amino, hydroxyl, hydroxylalkyl, substituted hydroxylalkyl, —C(O)$R^{12}$, —COO$R^{13}$, and O$R^{14}$, wherein $R^{12}$, $R^{13}$ and $R^{14}$ are independently selected from, for example, hydrogen, alkyl, substituted alkyl, aryl, substituted aryl, benzyl, substituted benzyl, benzoyl, substituted benzoyl, heteroalkyl, substituted heteroalkyl, heteroaryl, substituted heteroaryl, cycloalkyl, substituted cycloalkyl, heterocycloalkyl, substituted heterocycloalkyl, cycloalkenyl, substituted cycloalkenyl, alkenyl, substituted alkenyl, alkynyl, alkoxy, substituted alkoxy, acyl, sulfhydryl, halogen, amino, substituted amino, hydroxyl, hydroxylalkyl, and substituted hydroxylalkyl.

In one embodiment, the pentavalent derivatives of AST or AST-OH have a general structure of formula (II):

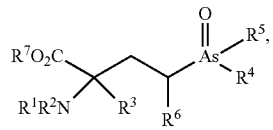

wherein $R^1$, $R^2$, $R^3$, $R^4$, $R^5$, $R^6$, and $R^7$ are independently selected from, for example, hydrogen, alkyl, substituted alkyl, aryl, substituted aryl, benzyl, substituted benzyl, benzoyl, substituted benzoyl, heteroalkyl, substituted heteroalkyl, heteroaryl, substituted heteroaryl, cycloalkyl, substituted cycloalkyl, heterocycloalkyl, substituted heterocycloalkyl, cycloalkenyl, substituted cycloalkenyl, alkenyl, substituted alkenyl, alkynyl, alkoxy, substituted alkoxy, acyl, sulfhydryl, halogen, amino, substituted amino, hydroxyl, hydroxylalkyl, substituted hydroxylalkyl and —COOH.

In one embodiment, the trivalent derivatives of AST or AST-OH have a general structure of formula (II'):

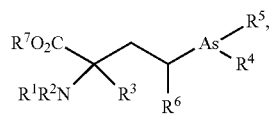

wherein $R^1$, $R^2$, $R^3$, $R^4$, $R^5$, $R^6$, and $R^7$ are independently selected from, for example, hydrogen, alkyl, substituted alkyl, aryl, substituted aryl, benzyl, substituted benzyl, benzoyl, substituted benzoyl, heteroalkyl, substituted heteroalkyl, heteroaryl, substituted heteroaryl, cycloalkyl, substituted cycloalkyl, heterocycloalkyl, substituted heterocycloalkyl, cycloalkenyl, substituted cycloalkenyl, alkenyl, substituted alkenyl, alkynyl, alkoxy, substituted alkoxy, acyl, sulfhydryl, halogen, amino, substituted amino, hydroxyl, hydroxylalkyl, substituted hydroxylalkyl and —COOH.

In one embodiment, $R^3$ and $R^6$ are hydrogen. In a further embodiment, the pentavalent derivatives of AST or AST-OH have a general structure of formula (III):

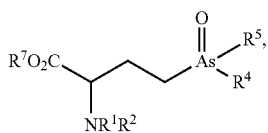

while the trivalent derivatives of AST or AST-OH have a general structure of formula (III'):

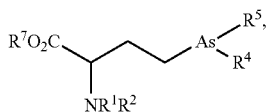

wherein $R^1$, $R^2$, $R^4$, $R^5$ and $R^7$ are independently selected from, for example, hydrogen, alkyl, substituted alkyl, aryl, substituted aryl, benzyl, substituted benzyl, benzoyl, substituted benzoyl, heteroalkyl, substituted heteroalkyl, heteroaryl, substituted heteroaryl, cycloalkyl, substituted cycloalkyl, heterocycloalkyl, substituted heterocycloalkyl, cycloalkenyl, substituted cycloalkenyl, alkenyl, substituted alkenyl, alkynyl, alkoxy, substituted alkoxy, acyl, sulfhydryl, halogen, amino, substituted amino, hydroxyl, hydroxylalkyl, substituted hydroxylalkyl and —COOH.

In one embodiment, $R^3$ and $R^6$ are hydrogen; and $R^5$ is methyl. In a further embodiment, the pentavalent derivatives of AST or AST-OH have a general structure of formula (IV):

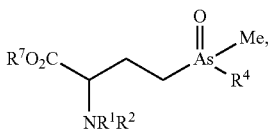

while the trivalent derivatives of AST or AST-OH have a general structure of formula (IV'):

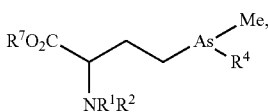

wherein $R^1$, $R^2$, $R^4$ and $R^7$ are independently selected from, for example, hydrogen, alkyl, substituted alkyl, aryl, substituted aryl, benzyl, substituted benzyl, benzoyl, substituted benzoyl, heteroalkyl, substituted heteroalkyl, heteroaryl, substituted heteroaryl, cycloalkyl, substituted cycloalkyl, heterocycloalkyl, substituted heterocycloalkyl, cycloalkenyl, substituted cycloalkenyl, alkenyl, substituted alkenyl, alkynyl, alkoxy, substituted alkoxy, acyl, sulfhydryl, halogen, amino, substituted amino, hydroxyl, hydroxylalkyl, substituted hydroxylalkyl and —COOH. In a further embodiment, $R^1$ and $R^2$ are independently selected from H, methyl, acetyl, $CF_3CO$, benzoyl and benzyl group; $R^4$ is methyl, ethyl, propyl, isopropyl, phenyl benzoyl, benzyl, sulthydryl or thiomethyl group; and $R^7$ is H, methyl, ethyl, propyl, isopropyl, phenyl, benzoyl, benzyl, or acetoxymethyl group.

In one embodiment, $R^3$ and $R^6$ are hydrogen; $R^4$ is $OR^{14}$; $R^5$ is methyl, wherein $R^{14}$ is selected from, for example, hydrogen, alkyl, substituted alkyl, aryl, substituted aryl, benzyl, substituted benzyl, benzoyl, substituted benzoyl, heteroalkyl, substituted heteroalkyl, heteroaryl, substituted heteroaryl, cycloalkyl, substituted cycloalkyl, heterocycloalkyl, substituted heterocycloalkyl, cycloalkenyl, substituted cycloalkenyl, alkenyl, substituted alkenyl, acyl, halogen, amino, substituted amino, hydroxylalkyl, and substituted hydroxylalkyl.

In a further embodiment, the pentavalent derivatives of AST or AST-OH have a general structure of formula (V):

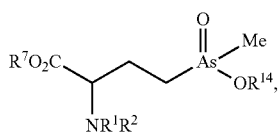

while the trivalent derivatives of AST or AST-OH have a general structure of formula (V'):

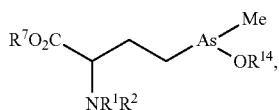

wherein $R^1$, $R^2$, $R^7$ and $R^{14}$ are independently selected from, for example, hydrogen, alkyl, substituted alkyl, phenyl, substituted phenyl, benzyl, substituted benzyl, benzoyl, substituted benzoyl, heteroalkyl, substituted heteroalkyl, acetyl, and amino.

In specific embodiments, $R^1$ and $R^2$ are independently selected from H, methyl, acetyl, $CF_3CO$, benzoyl and benzyl group; $R^7$ and $R^{14}$ are independently selected from H, methyl, ethyl, propyl, isopropyl, phenyl, benzoyl, benzyl, and acetoxymethyl group.

In one embodiment, $R^1$, $R^2$, $R^3$, $R^6$, and $R^7$ are hydrogen; and $R^4$ is —OH. In a further embodiment, the pentavalent derivatives of AST or AST-OH have a general structure of formula (VI):

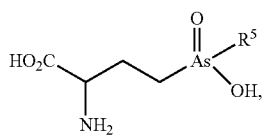

while the trivalent derivatives of AST or AST-OH have a general structure of formula (VI'):

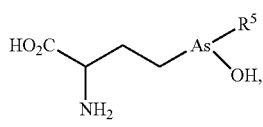

wherein $R^5$ is alkyl, $CH_2NH_2$ or OH.

In one embodiment, the pentavalent derivatives of AST or AST-OH have a general structure of formula (VII):

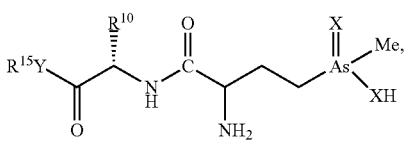

while the trivalent derivatives of AST or AST-OH have a general structure of formula (VII'):

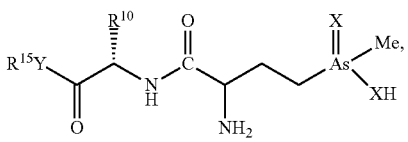

wherein X is O or S; $R^{10}$ is methyl, ethyl, propyl, isopropyl, $CH_2Ph$, or an aromatic group; Y is N or O; and $R^{15}$ is hydrogen, alkyl, substituted alkyl, aryl, substituted aryl, benzyl, substituted benzyl, benzoyl, substituted benzoyl, heteroalkyl, substituted heteroalkyl, heteroaryl, substituted heteroaryl, cycloalkyl, substituted cycloalkyl, heterocycloalkyl, substituted heterocycloalkyl, cycloalkenyl, substituted cycloalkenyl, alkenyl, substituted alkenyl, acyl, halogen, amino, substituted amino, hydroxylalkyl, and substituted hydroxylalkyl.

In a further embodiment, Y is O, and $R^{15}$ is alkyl, $CH_2Ph$ or an aromatic group. In a specific embodiment, Y is O; and $R^{15}$ is methyl, ethyl, propyl, isopropyl, acetoxymethyl, phenyl, $CH_2Ph$ or benzyl.

In some embodiments, $R^{15}Y$ may be acetoxymethyl ester, an amino acid, e.g., Ala, Leu, or Val, or a short peptide comprising at least two amino acids, e.g., Ala-Ala, Ala-Leu, Ala-Ala-Ala, when Y is the amino group of the corresponding amino acid. In specific embodiments, the short peptide comprises n amino acids, wherein $2 \leq n \leq 20$, $2 \leq n \leq 5$, $2 \leq n \leq 10$, or $2 \leq n \leq 5$.

In specific embodiments, the pentavalent derivative of AST or AST-OH is

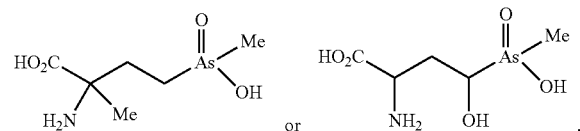

The trivalent derivatives of AST or AST-OH is

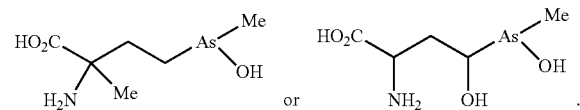

The recitation of a listing of chemical groups in any definition of a variable herein includes definitions of that variable as any single group or combination of listed groups. The recitation of an embodiment for a variable or aspect herein includes that embodiment as any single embodiment or in combination with any other embodiments or portions thereof.

In one embodiment, the derivatives of AST and/or AST-OH of the subject invention do not include AST and AST-OH. In one embodiment, when X is O; $R^1$, $R^2$, $R^3$ and $R^6$ are hydrogen; Z is $OR^7$, wherein $R^7$ is hydrogen; $R^4$ is $OR^{14}$, wherein $R^{14}$ is hydrogen; $R^5$ cannot be alkoxy or methyl. In one embodiment, when X is O; $R^1$, $R^2$, $R^3$ and $R^6$ are hydrogen; Z is $OR^7$, wherein $R^7$ is hydrogen; $R^5$ is $OR^{14}$, wherein $R^{14}$ is hydrogen; $R^4$ cannot be alkoxy or methyl.

Method of Treatment

Certain embodiments of the subject invention provide methods of treating an infection in a subject caused by an infectious agent, preferably, other than *E. coli*, the method comprising administering to the subject AST, AST-OH, and/or derivatives, or salts thereof. AST, AST-OH, and/or derivatives, or salts thereof can be administered in the form of a pharmaceutical composition comprising pharmaceutically acceptable carriers.

The infectious agent can be a bacterium, protozoan, helminth, archaebacterial, or a fungus. Preferably, the infectious agent expresses glutamine synthetase. In certain embodiments, the infectious agent expresses phosphinothricin N-acetyltransferase or arsinothricin N-acetyltransferase, and the method further comprises administering to the subject an inhibitor of phosphinothricin N-acetyltransferase or arsinothricin N-acetyltransferase.

AST, AST-OH, and/or derivatives, or salts thereof can be administered via, for example, oral, pulmonary, buccal, suppository, intravenous, intraperitoneal, intranasal, intramuscular or subcutaneous routes. Additional routes of administration are well known to a skilled artisan and such embodiments are within the purview of this invention. The appropriate route of administration depends on the type of infection being treated, the subject being treated, the stage and severity of the infection, etc. A person of ordinary skill in the art can determine an appropriate route of administration based on specific parameters.

A bacterium can be Gram-positive or Gran-negative. Non-limiting examples of bacterial infections that can be treated according to the methods of the invention include infections caused by *Burkolderia* spp., *Sinorhizobium* spp., *Schewanella* spp., *Bacillus* spp., *Corynebacterium* spp., *Mycobacterium* spp., and *Enterobacter* spp. Specific bacterial species include *Burkolderia gladioli, Sinorhizobium meliloti, Schewanella putrefaciens, Bacillus cereus, Bacillus megaterium, Corynebacterium glutamicum, Mycobacterium bovis, Mycobacterium tuberculosis*, and *Enterobacter cloacae*.

In preferred embodiments the invention provides methods of treating an infection caused by *Mycobacterium tuberculosis, Mycobacterium bovis*, or carbapenem-resistant *Enterobacter cloacae*. In other preferred embodiments, the invention provides methods of treating an infection caused by carbapenem-resistant *Acinetobacter baumannii*, carbapenem-resistant *Pseudomonas aeruginosa*, carbapenem-resistant Enterobacteriaceae (including *Enterobacter cloacae*), vancomycin-resistant *Enterococcus faecium*, methicillin- and/or vancomycin-resistant *Staphylococcus aureus*, clarithromycin-resistant *Helicobacter pylori*, fluoroquinolone-resistant *Campylobacter* spp., fluoroquinolone-resistant Salmonellae, cephalosporin and/or fluoroquinolone-resistant *Neisseria gonorrhoeae*, penicillin-non-susceptible *Streptococcus pneumoniae*, ampicillin-resistant *Haemophilus influenzae*, fluoroquinolone-resistant *Shigella* spp. or carbapenem-resistant *Enterobacter cloacae*.

Specific examples of inhibitors of phosphinothricin N-acetyltransferase or arsinothricin N-acetyltransferase include 2-({8-fluoro-5H-pyridazino[4,5-b]indol-4-yl}sulfanyl)-N-(1,2,3,4-tetrahydronaphthalen-1-yl)acetamide; 3-oxo-N-({1-phenyl-1H,4H,5H,6H-cyclopenta[c]

pyrazol-3-yl}methyl)-3,4-dihydro-2H-1,4-benzothiazine-6-carboxamide; 1-(4-fluorobenzoyl)-N-(3-phenyl-1H-pyrazol-4-yl)piperidine-3-carboxamide; N-[3-({[(6-fluoro-3,4-dihydro-2H-1-benzopyran-4-yl)carbamoyl]amino}methyl)phenyl]cyclobutanecarboxamide; and 1-[1-(2-fluorobenzoyl)piperidin-4-yl]-3-[2-(3-fluorophenyl)cyclopropyl]urea.

Further embodiments of the invention provide a method of killing or inhibiting the growth of an infectious agent, preferably, other than *E. coli*, the method comprising contacting the infectious agent with an effective amount of AST, AST-OH, and/or derivatives, or salts thereof. Specific infectious agents discussed in connection with the methods of treating infections in a subject can be killed or inhibited according to the methods disclosed herein.

Additional embodiments of the invention provide a composition comprising AST, AST-OH, and/or derivatives, or salts thereof and a pharmaceutically acceptable carrier. Specific inhibitors of phosphinothricin N-acetyltransferase or arsinothricin N-acetyltransferase identified above can be used in the compositions of the invention. In certain embodiments, the compositions comprising AST, AST-OH, and/or derivatives, or salts thereof, an inhibitor of phosphinothricin N-acetyltransferase or arsinothricin N-acetyltransferase, and a pharmaceutically acceptable carrier or excipient.

Routes of Administration and Dosage Forms

In certain embodiments, the composition of the subject invention comprising AST, AST-OH, and/or a derivative, or salt thereof, may be administered intramuscularly, subcutaneously, intrathecally, intravenously or intraperitoneally by infusion or injection. Solutions of AST, AST-OH, and/or a derivative, or salt thereof, can be prepared in water, optionally mixed with a nontoxic surfactant. Under ordinary conditions of storage and use, these preparations can contain a preservative to prevent the growth of microorganisms.

The pharmaceutical dosage forms suitable for injection or infusion can include sterile aqueous solutions or dispersions or sterile powders comprising AST, AST-OH, and/or a derivative, or salt thereof, which are adapted for the extemporaneous preparation of sterile injectable or infusible solutions or dispersions, optionally encapsulated in liposomes. Preferably, the ultimate dosage form should be sterile, fluid, and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof.

The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers, or sodium chloride. Prolonged absorption of the injectable compositions can be brought about by the use in the compositions of agents delaying absorption, for example, aluminum monostearate and gelatin.

Sterile injectable solutions are prepared by incorporating AST, AST-OH, and/or a derivative, or salt thereof, in the required amount in the appropriate solvent as described herein with various of the other ingredients enumerated herein, as required, preferably followed by filter sterilization. In the case of sterile powders for the preparation of sterile injectable solutions, the preferred methods of preparation are vacuum drying and freeze drying techniques, which yield a powder of AST, AST-OH, and/or derivative, or salt thereof, plus any additional desired ingredient present in the previously sterile-filtered solutions.

The compositions of the subject invention may also be administered orally, in combination with a pharmaceutically acceptable vehicle such as an inert diluent or an assimilable edible carrier. They may be enclosed in hard or soft shell gelatin capsules, or may be compressed into tablets.

For oral therapeutic administration, AST, AST-OH, and/or derivative, or salt thereof may be combined with one or more excipients and used in the form of ingestible tablets, buccal tablets, troches, capsules, elixirs, suspensions, syrups, wafers, and the like. Such compositions and preparations should contain at least 0.1% of AST, AST-OH, and/or derivatives, or salts thereof of the present invention. The percentage of AST, AST-OH, and/or derivatives, or salts thereof present in such compositions and preparations may, of course, be varied and may conveniently be between about 2% to about 60% of the weight of a given unit dosage form. The amount of AST, AST-OH, and/or derivatives, or salts thereof in such therapeutically useful compositions is such that an effective dosage level will be obtained.

The tablets, troches, pills, capsules, and the like may also contain one or more of the following: binders such as gum tragacanth, acacia, corn starch or gelatin; excipients such as dicalcium phosphate; a disintegrating agent such as corn starch, potato starch, alginic acid, and the like; a lubricant such as magnesium stearate; and a sweetening agent such as sucrose, fructose, lactose, or aspartame, or a flavoring agent such as peppermint, oil of wintergreen, or cherry flavoring may be added.

When the unit dosage form is a capsule, it may contain, in addition to materials of the above type, a liquid carrier, such as a vegetable oil or a polyethylene glycol.

Various other materials may be present as coatings or for otherwise modifying the physical form of the solid unit dosage form. For instance, tablets, pills, or capsules may be coated with gelatin, wax, shellac, or sugar, and the like.

Of course, any material used in preparing any unit dosage form should be pharmaceutically acceptable and substantially non-toxic in the amounts employed.

In addition, AST, AST-OH, and/or derivatives, or salts thereof may be incorporated into sustained-release preparations and devices. For example, AST, AST-OH, and/or derivatives, or salts thereof may be incorporated into time release capsules, time release tablets, time release pills, and time release polymers or nanoparticles.

Pharmaceutical compositions for topical administration of AST, AST-OH, and/or derivatives, or salts thereof to the epidermis (mucosal or cutaneous surfaces) can be formulated as ointments, creams, lotions, gels, or as a transdermal patch. Such transdermal patches can contain penetration enhancers such as linalool, carvacrol, thymol, citral, menthol, t-anethole, and the like. Ointments and creams can, for example, include an aqueous or oily base with the addition of suitable thickening agents, gelling agents, colorants, and the like. Lotions and creams can include an aqueous or oily base and typically also contain one or more emulsifying agents, stabilizing agents, dispersing agents, suspending agents, thickening agents, coloring agents, and the like. Gels preferably include an aqueous carrier base and include a gelling agent such as cross-linked polyacrylic acid polymer, a derivatized polysaccharide (e.g., carboxymethyl cellulose), and the like.

Pharmaceutical compositions suitable for topical administration in the mouth (e.g., buccal or sublingual administration) include lozenges comprising the composition in a flavored base, such as sucrose, acacia, or tragacanth; pastilles comprising the composition in an inert base such as gelatin and glycerin or sucrose and acacia; and mouthwashes comprising the active ingredient in a suitable liquid carrier. The pharmaceutical compositions for topical administration in the mouth can include penetration enhancing agents, if desired.

Useful solid carriers include finely divided solids such as talc, clay, microcrystalline cellulose, silica, alumina, and the like. Other solid carriers include nontoxic polymeric nanoparticles or microparticles. Useful liquid carriers include water, alcohols, or glycols, or water/alcohol/glycol blends, in which AST, AST-OH, and/or derivatives, or salts thereof can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers.

Thickeners such as synthetic polymers, fatty acids, fatty acid salts and esters, fatty alcohols, modified celluloses, or modified mineral materials can also be employed with liquid carriers to form spreadable pastes, gels, ointments, soaps, and the like, for application directly to the skin of the user.

The concentration of AST, AST-OH, and/or derivatives, or salts thereof in such formulations can vary widely depending on the nature of the formulation and intended route of administration. For example, the concentration of AST, AST-OH, and/or derivatives, or salts thereof, in a liquid composition, such as a lotion, can preferably be from about 0.1-25% by weight, or, more preferably, from about 0.5-10% by weight. The concentration in a semi-solid or solid composition such as a gel or a powder can preferably be about 0.1-5% by weight, or, more preferably, about 0.5-2.5% by weight.

Pharmaceutical compositions for spinal administration or injection into amniotic fluid can be provided in unit dose form in ampoules, pre-filled syringes, small volume infusion, or in multi-dose containers, and can include an added preservative. The compositions for parenteral administration can be suspensions, solutions, or emulsions, and can contain excipients such as suspending agents, stabilizing agents, and dispersing agents.

A pharmaceutical composition suitable for rectal administration comprises AST, AST-OH, and/or a derivative, or salt thereof, and further in combination with a solid or semisolid (e.g., cream or paste) carrier or vehicle. For example, such rectal compositions can be provided as unit dose suppositories. Suitable carriers or vehicles include cocoa butter and other materials commonly used in the art.

According to one embodiment, pharmaceutical compositions of the present invention suitable for vaginal administration are provided as pessaries, tampons, creams, gels, pastes, foams, or sprays containing AST, AST-OH, and/or a derivative, or salt thereof in further combination with carriers known in the art. Alternatively, compositions suitable for vaginal administration can be delivered in a liquid or solid dosage form.

Pharmaceutical compositions suitable for intra-nasal administration are also encompassed by the present invention. Such intra-nasal compositions comprise AST, AST-OH, and/or a derivative, or salt thereof in a vehicle and suitable administration device to deliver a liquid spray, dispersible powder, or drops. Drops may be formulated with an aqueous or non-aqueous base also comprising one or more dispersing agents, solubilizing agents, or suspending agents. Liquid sprays are conveniently delivered from a pressurized pack, an insufflator, a nebulizer, or other convenient means of delivering an aerosol comprising AST, AST-OH, and/or a derivative, or salt thereof. Pressurized packs comprise a suitable propellant such as dichlorodifluoromethane, trichlorofluoromethane, dichlorotetrafluoroethane, carbon dioxide, or other suitable gas as is well known in the art. Aerosol dosages can be controlled by providing a valve to deliver a metered amount of AST, AST-OH, and/or derivatives, or salts thereof.

AST, AST-OH, and/or derivatives, or salts thereof may be combined with an inert powdered carrier and inhaled by the subject or insufflated. Pharmaceutical compositions for administration by inhalation or insufflation can be provided in the form of a dry powder composition, for example, a powder mix of AST, AST-OH, and/or derivatives, or salts thereof, and a suitable powder base such as lactose or starch. Such powder composition can be provided in unit dosage form, for example, in capsules, cartridges, gelatin packs, or blister packs, from which the powder can be administered with the aid of an inhalator or insufflator.

The exact amount (effective dose) of AST, AST-OH, and/or derivatives, or salts thereof can vary from subject to subject, depending on, for example, the species, age, weight, and general or clinical condition of the subject, the severity or mechanism of any disorder being treated, the particular agent or vehicle used, the method and scheduling of administration, and the like. A therapeutically effective dose can be determined empirically, by conventional procedures known to those of skill in the art. See, e.g., The Pharmacological Basis of Therapeutics, Goodman and Gilman, eds., Macmillan Publishing Co., New York. For example, an effective dose can be estimated initially either in cell culture assays or in suitable animal models. The animal model may also be used to determine the appropriate concentration ranges and routes of administration. Such information can then be used to determine useful doses and routes for administration in humans. Methods for the extrapolation of effective dosages in mice and other animals to humans are known to the art; for example, see U.S. Pat. No. 4,938,949, which is hereby incorporated by reference. A therapeutic dose can also be selected by analogy to dosages for comparable therapeutic agents.

The particular mode of administration and the dosage regimen will be selected by the attending clinician, taking into account the particulars of the case (e.g., the subject, the disease, the disease state involved, and whether the treatment is prophylactic). Treatment may involve daily or multi-daily doses of compound(s) over a period of a few days to months, or even years.

In general, however, a suitable dose will be in the range of from about 0.001 to about 100 mg/kg of body weight per day, preferably from about 0.01 to about 100 mg/kg of body weight per day, more preferably, from about 0.1 to about 50 mg/kg of body weight per day, or even more preferred, in a range of from about 1 to about 10 mg/kg of body weight per day. For example, a suitable dose may be about 1 mg/kg, 10 mg/kg, or 50 mg/kg of body weight per day.

AST, AST-OH, and/or derivatives, or salts thereof can be conveniently administered in unit dosage form, containing for example, about 0.05 to about 10000 mg, about 0.5 to about 10000 mg, about 5 to about 1000 mg, or about 50 to about 500 mg of each of AST, AST-OH, and/or derivatives, or salts thereof.

AST, AST-OH, and/or derivatives, or salts thereof can be administered to achieve peak plasma concentrations of, for example, from about 0.25 to about 200 µM, about 0.5 to about 75 µM, about 1 to about 50 µM, about 2 to about 30

μM, or about 5 to about 25 μM of each of AST, AST-OH, and/or derivatives, or salts thereof per unit dosage form. Exemplary desirable plasma concentrations include at least 0.25, 0.5, 1, 5, 10, 25, 50, 75, 100 or 200 μM. For example, plasma levels may be from about 1 to about 100 micromolar or from about 10 to about 25 micromolar. This may be achieved, for example, by the intravenous injection of a 0.05 to 5% solution of AST, AST-OH, and/or derivatives, or salts thereof, optionally in saline, or orally administered as a bolus containing about 1 to about 100 mg of AST, AST-OH, and/or derivatives, or salts thereof. Desirable blood levels may be maintained by continuous or intermittent infusion.

AST, AST-OH, and/or derivatives, or salts thereof can be included in the compositions within a therapeutically useful and effective concentration range, as determined by routine methods that are well known in the medical and pharmaceutical arts. For example, a typical composition can include AST, AST-OH, and/or derivatives, or salts thereof, at a concentration in the range of at least about 1 mg/ml, preferably at least about 4 mg/ml, more preferably at least 5 mg/ml and most preferably at least 6 mg/ml of each of AST, AST-OH, and/or derivatives, or salts thereof.

AST, AST-OH, and/or derivatives, or salts thereof may conveniently be presented in a single dose or as divided doses administered at appropriate intervals, for example, as one dose per day or as two, three, four or more sub-doses per day. The sub-dose itself may be further divided, e.g., into a number of discrete loosely spaced administrations; such as multiple inhalations from an insufflator.

Optionally, the pharmaceutical compositions of the present invention can include one or more other therapeutic agents, e.g., as a combination therapy. The additional therapeutic agent(s) will be included in the compositions within a therapeutically useful and effective concentration range, as determined by routine methods that are well known in the medical and pharmaceutical arts. The concentration of any particular additional therapeutic agent may be in the same range as is typical for use of that agent as a monotherapy, or the concentration may be lower than a typical monotherapy concentration if there is a synergy when combined with AST, AST-OH, and/or derivatives, or salts thereof.

EXAMPLES

Materials and Methods
Synthetic Procedures and Characterization Data for Compounds General Information. $^1$H NMR spectra at 400 MHz and $^{13}$C NMR at 100.6 MHz were recorded in $D_2O$ unless otherwise noted. All chemical shift values are reported in parts per million (ppm) and referenced to the residual solvent peaks of DMSO-$d_6$ (2.5 ppm), CDCl$_3$ (7.26) and $D_2O$ (4.79 ppm) for $^1$H NMR and the DMSO-$d_6$ (39.52 ppm) or CDCl$_3$ (77.16) peaks for $^{13}$C NMR spectra, with coupling constant (J) values reported in Hz. HRMS were obtained in TOF (ESI) negative mode. TLC was performed on Merck Kieselgel 60-F$_{254}$, and products were detected with 254 nm light. Merck Kieselgel 60 (230-400 mesh) was used for column chromatography. All reagents and solvents were purchased from commercial suppliers and used without further purification.

Figure 4A:
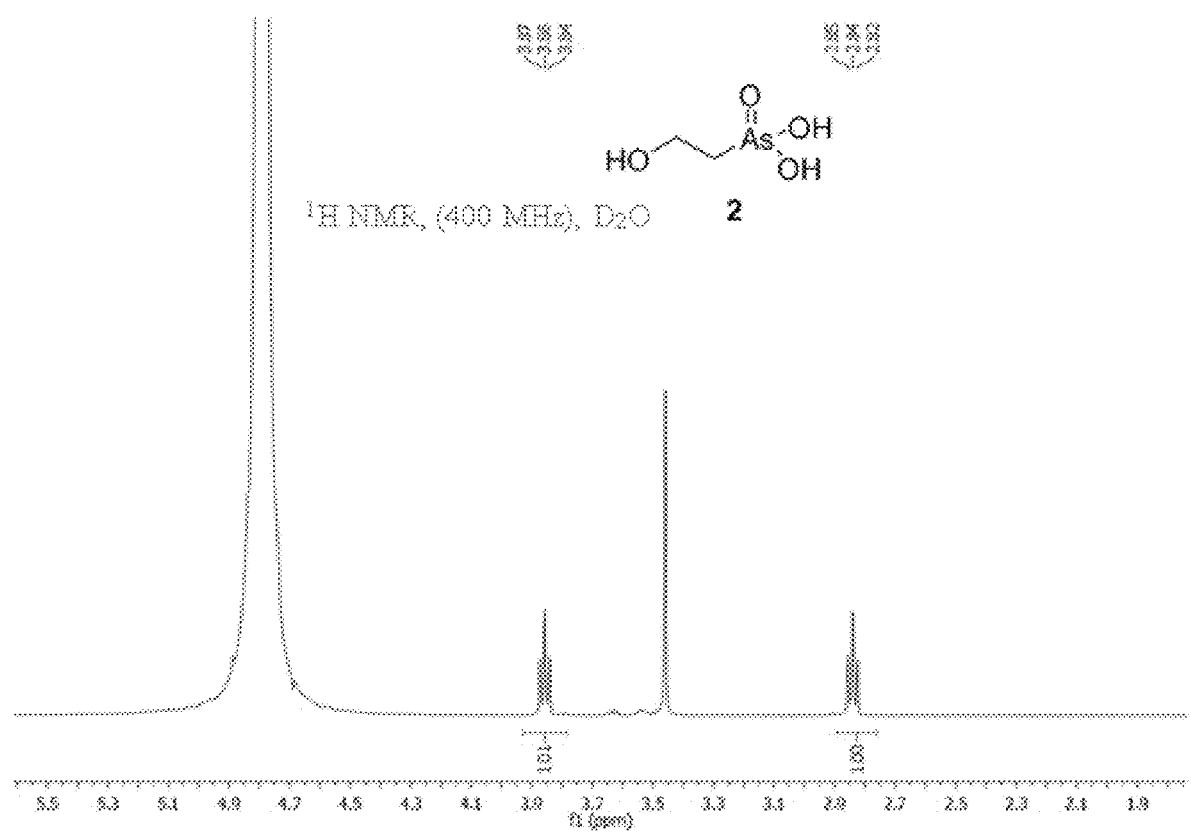
FIGS. 4A-4B show the NMR data of compound 2.
Figure 4B:
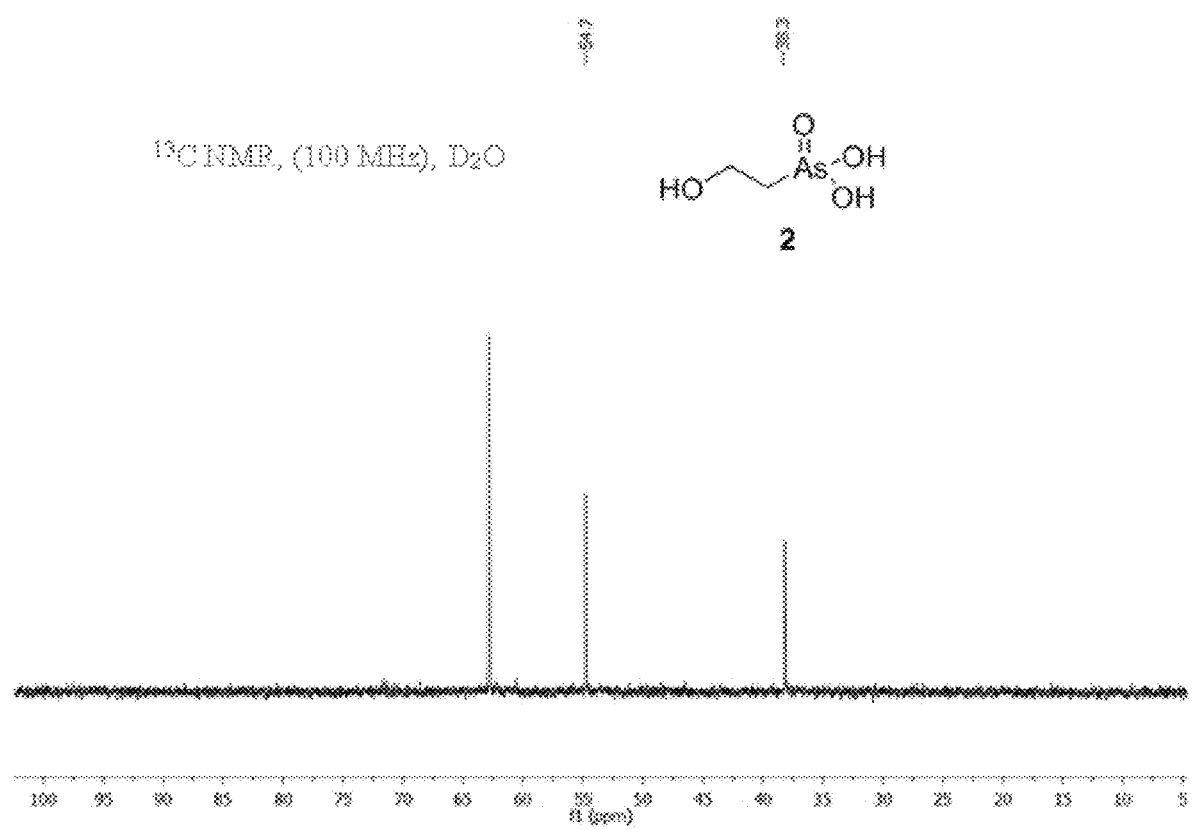

(2-Hydroxyethyl)arsonic acid (2). 12 M aqueous NaOH (155 mL, 74.5 g, 1.86 mol) was slowly added with stirring into the cooled (ice-bath) suspension of As$_2$O$_3$ (62.5 g, 0.31 mol) in H$_2$O (100 mL) in a round bottom flask over 20 min. Then 2-chloroethanol (1; 42 mL, 50 g, 0.621 mol) was slowly added into the resulting homogeneous mixture so that temperature did not rise above 20° C. The reaction mixture was stirred at 20° C. for 30 min and then at ambient temperature for 12 h. The white precipitate of NaCl was removed by vacuum filtration. Evaporation of volatiles from the filtrate at reduced pressure afforded the disodium salt of crude 2 (115 g, 86%) as a white solid: $^1$H NMR (D$_2$O) δ 2.84 (t, J=6.2 Hz, 2H), 3.86 (t, J=6.2 Hz, 2H) (FIG. 4A); $^{13}$C NMR (D$_2$O) δ 39.2, 54.7 (FIG. 4B); HRMS calcd for C$_2$H$_6$AsO$_4$ [M-H]$^-$ 168.9487, found 168.9483.

Figure 5A:
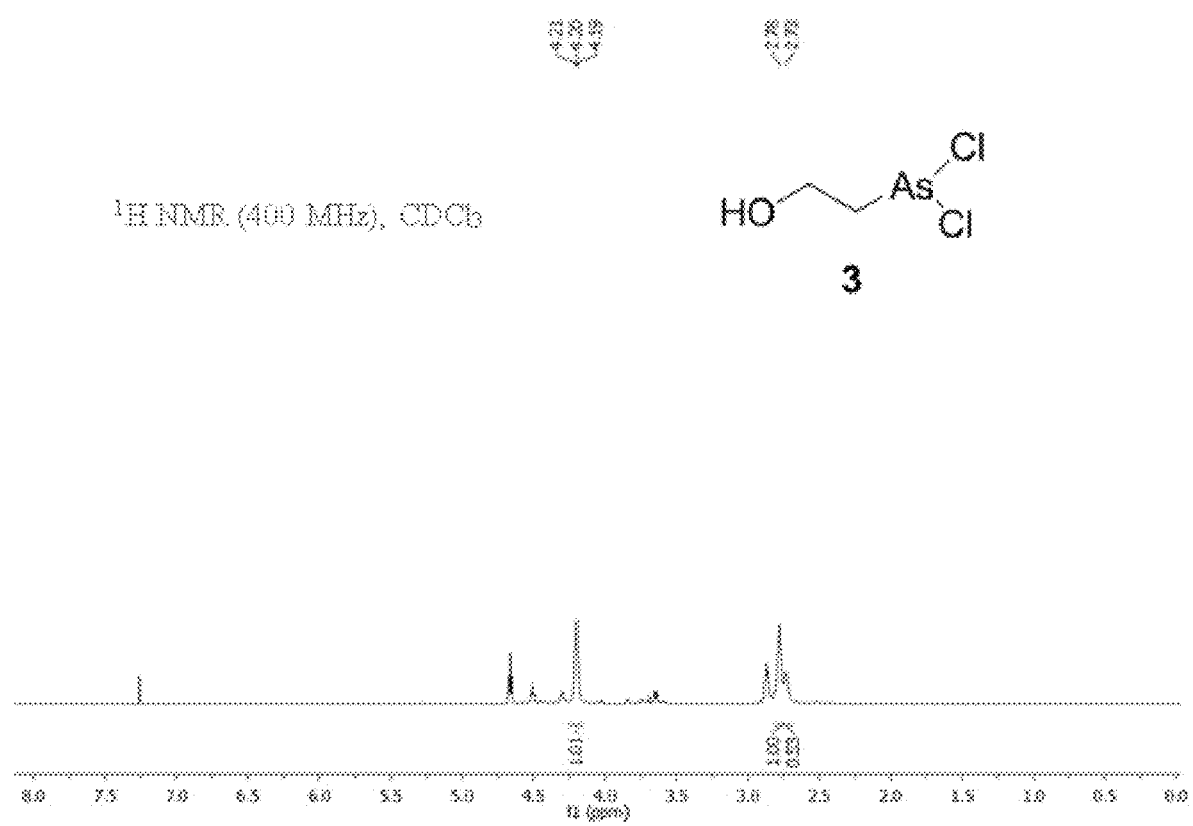
FIGS. 5A-5B show the NMR data of compound 3.
Figure 5B:
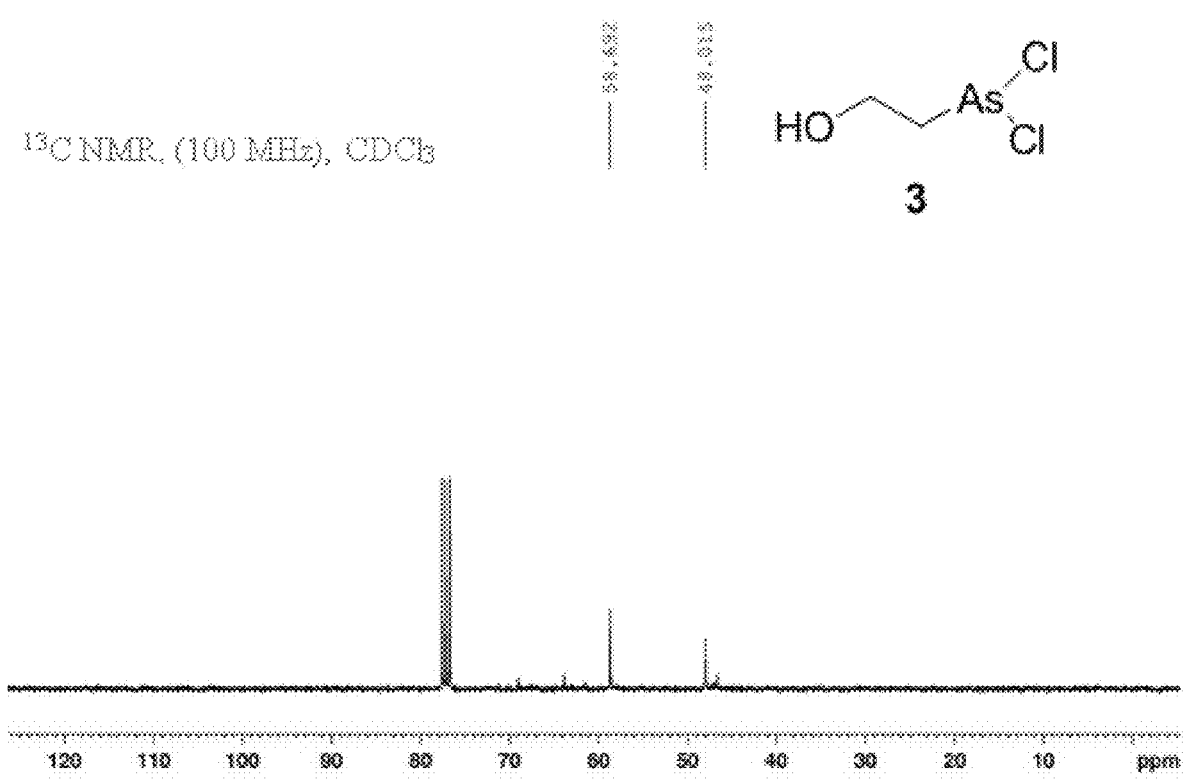

(2-Chloroethyl)arsonic acid (5). Method A (Step a). Conc. HCl (500 mL) was slowly added into the stirring solution of crude 2 (70 g, 0.33 mol; dissolved in 130 mL H$_2$O) over 10 min. A catalytic amount of KI (500 mg, 3 mmol) was then added, and SO$_2$ gas (1.0 mol) was bubbled into the solution for 1 h with continuous stirring. The resulting mixture was extracted with dichloromethane (3×100 mL) and dried over anhydrous Na$_2$SO$_4$. The volatiles were evaporated under reduced pressure to afford dichloro(2-hydroxyethyl)arsine 3 (59.3 g, 94%) as a yellowish oil: $^1$H NMR (CDCl$_3$) δ 2.78 (t, J=6.5 Hz, 2H), 4.2 (t, J=6.1 Hz, 2H) (FIG. 5A); $^{13}$C NMR (CDCl$_3$) δ 48.0, 58.7 (FIG. 5B).

Figure 6A:
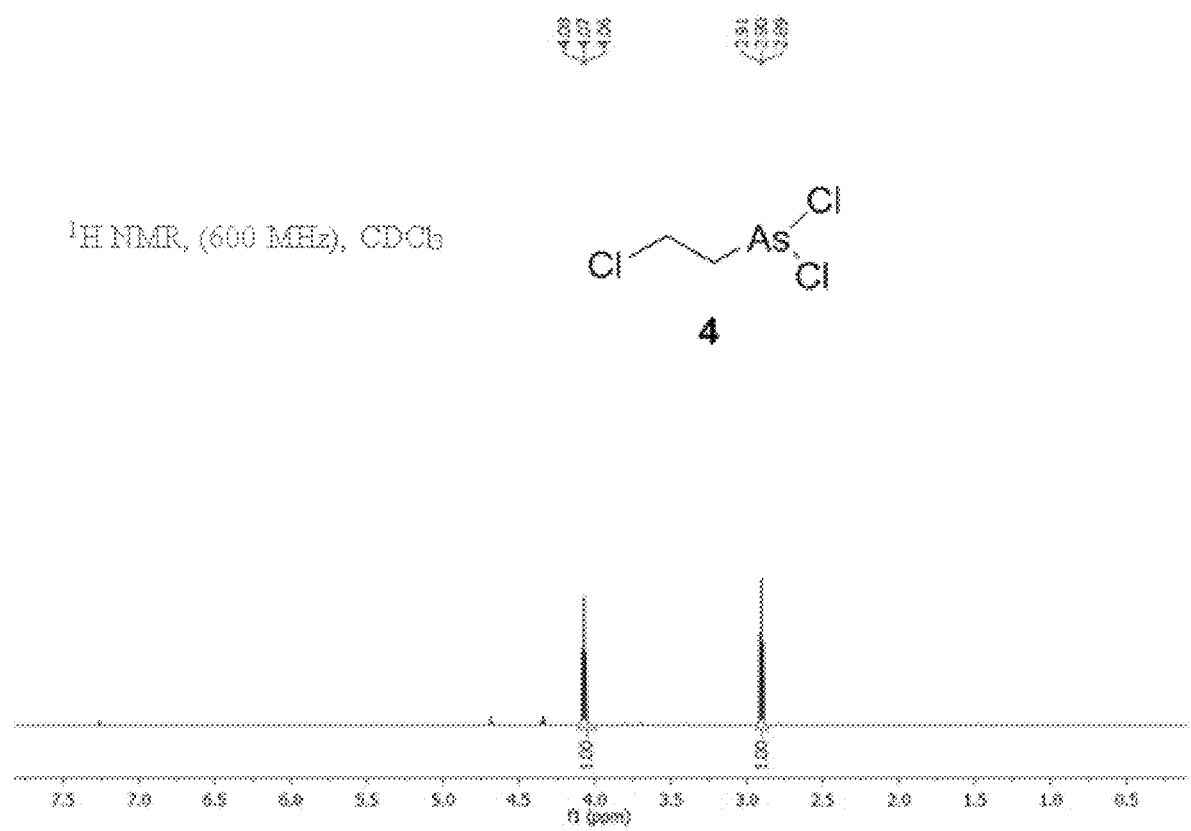
FIGS. 6A-6B show the NMR data of compound 4.
Figure 6B:
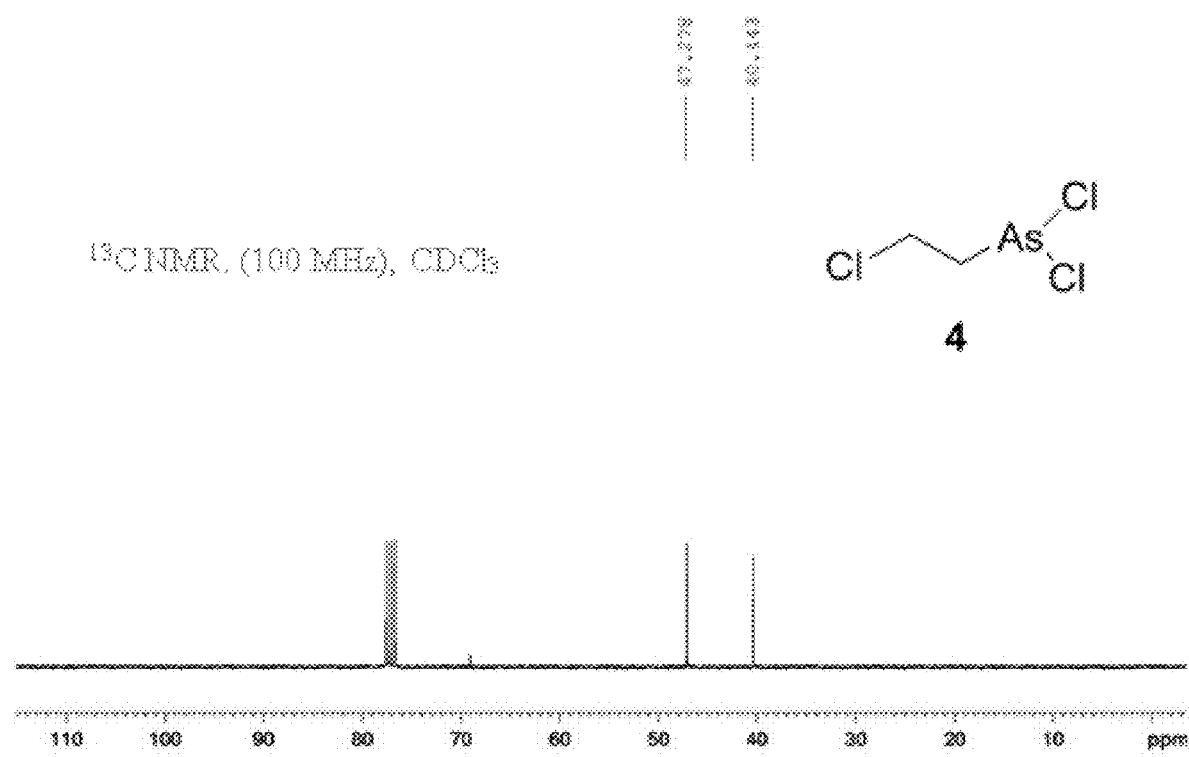

(Step b). Anhydrous CHCl$_3$ (60 mL) was added into a flask containing 3 (40 g, 0.21 mol), and the resulting solution was stirred for 20 min at 0° C. (ice-bath). Next SOCl$_2$ (38 mL, 62.4 g, 0.525 mol) was slowly added over 20 min with continuous stirring. The resulting mixture was allowed to warm to ambient temperature (1 h), and stirring was continued for 12 h. The resulting mixture was concentrated under reduced pressure at ambient temperature, and distilled at (110-120° C.) under reduced pressure (water vacuum, 16 mmHg) to yield dichloro(2-chloroethyl)arsine 4 (27.9 g, 64.7%) as a light pink liquid: $^1$H NMR (CDCl$_3$) δ 2.90 (t, J=7.2 Hz, 2H), 4.07 (t, J=7.2 Hz, 2H) (FIG. 6A); $^{13}$C NMR (CDCl$_3$) δ 40.4, 47.3 (FIG. 6B).

Figure 7A:
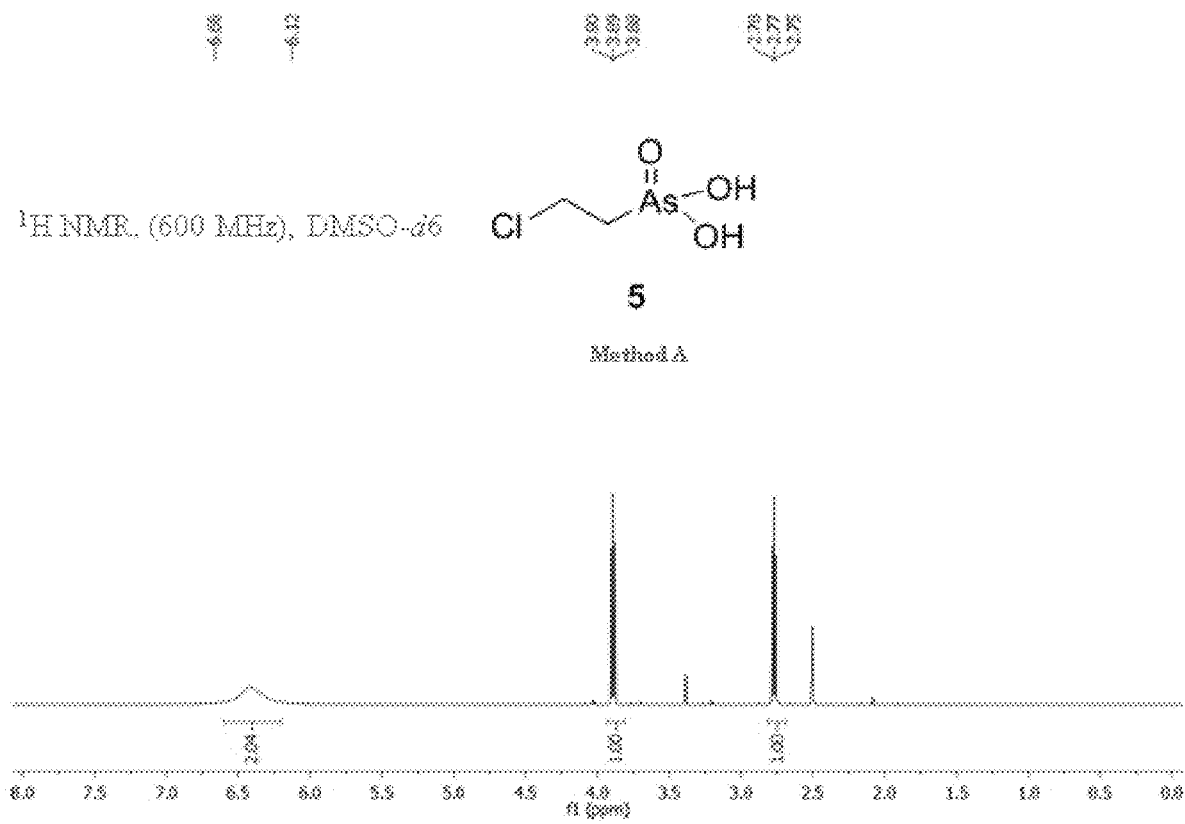
FIGS. 7A-7C show the NMR data of compound 5.
Figure 7B:
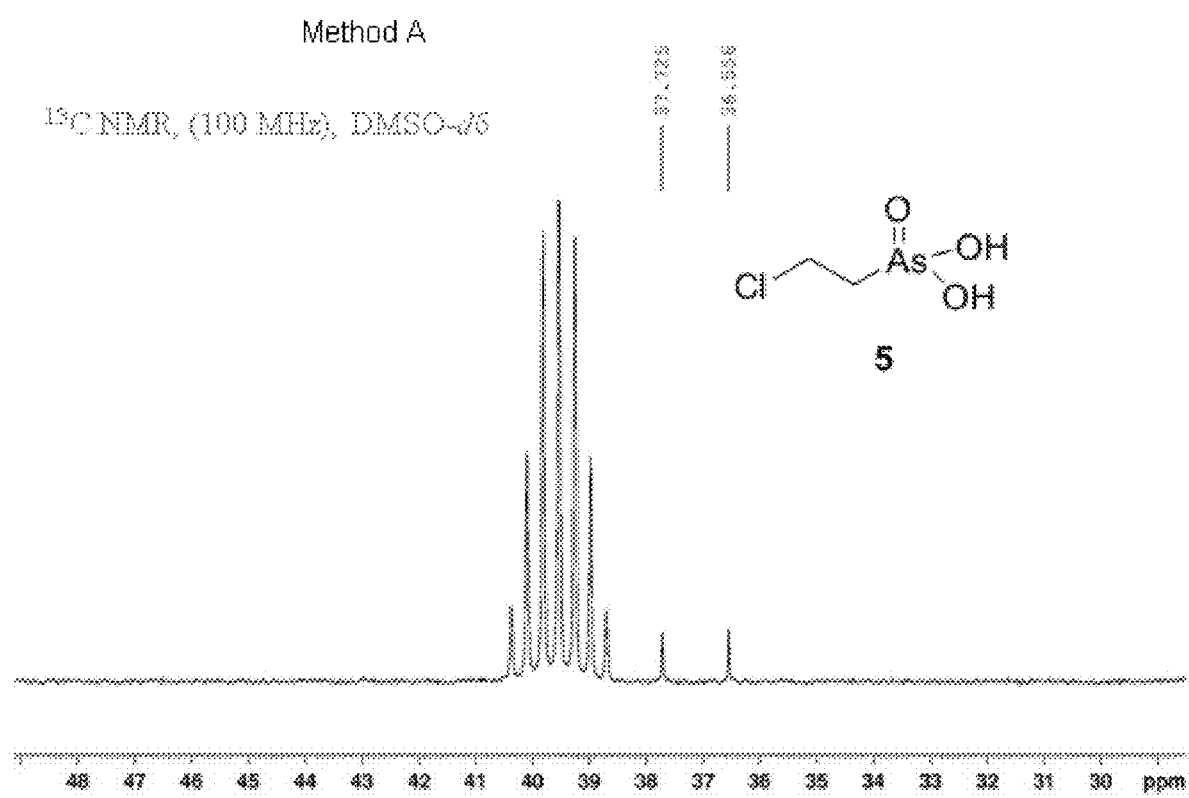

(Step c) Compound 4 (22 g, 0.11 mol) was suspended in 100 mL of H$_2$O, and the suspension was placed in an ice-bath for 20 min. H$_2$O$_2$ (42 mL 30% aqueous solution) was slowly added into the suspension (0° C., ice-bath) with continuous stirring for 20 min. The resulting solution was allowed to warm to ambient temperature (1 h) with continuous stirring. Volatiles were evaporated under reduced pressure at approximately 50° C., and the residue was dissolved in 15 mL hot acetone (~45° C.). The product was crystallized by adding diethyl ether (10 mL) and cooled in ice-bath for 30 min. Vacuum filtration afforded 5 (13.4 g, 64.8%) as a white solid: $^1$H NMR (DMSO-d$_6$) δ 2.77 (t, J=7.5 Hz, 2H), 3.89 (t, J=8.1 Hz, 2H), 6.40-6.45 (br, 2H) (FIG. 7A); $^{13}$C NMR (DMSO-d$_6$) δ 36.6, 37.7 (FIG. 7B); HRMS calcd for C$_2$H$_5$AsClO$_3$ [M-H]$^-$ 186.9149, found 186.9149.

Method B. 6 M aqueous NaOH (100 mL, 24 g, 0.6 mol) was added over 20 min into the cooled (ice-bath) suspension of As$_2$O$_3$ (20.1 g, 0.1 mol) in H$_2$O (50 mL) in a round bottom flask with continuous stirring. Then 1,2-dichloroethane (9; 16 mL, 20 g, 0.2 mol) was slowly added into the resulting homogeneous mixture. The reaction mixture was stirred at 60° C. for 48 h with continuous stirring. The mixture was then concentrated to 100 mL at reduced pressure and the pH of the solution was adjusted to ~2.0 with 4 M HCl. The off-white precipitate was removed by vacuum filtration. Evaporation of volatiles from the filtrate at reduced pressure gave 30 g of a white solid, which was suspended in isopropyl alcohol. The white precipitate was removed by vacuum filtration. Evaporation of volatiles from the filtrate at reduced pressure afforded crude 5 (3.0 g, 12.8%) as a transparent gummy solid containing ~10% of the vinylarsonic acid: $^1$H NMR (600 MHz, D$_2$O) δ 4.06 (t, J=6.4 Hz, 2H), 2.88 (t, J=6.4 Hz, 2H); 6.48 (d, J=18.4 Hz, 0.1H), 6.56

Figure 7C:
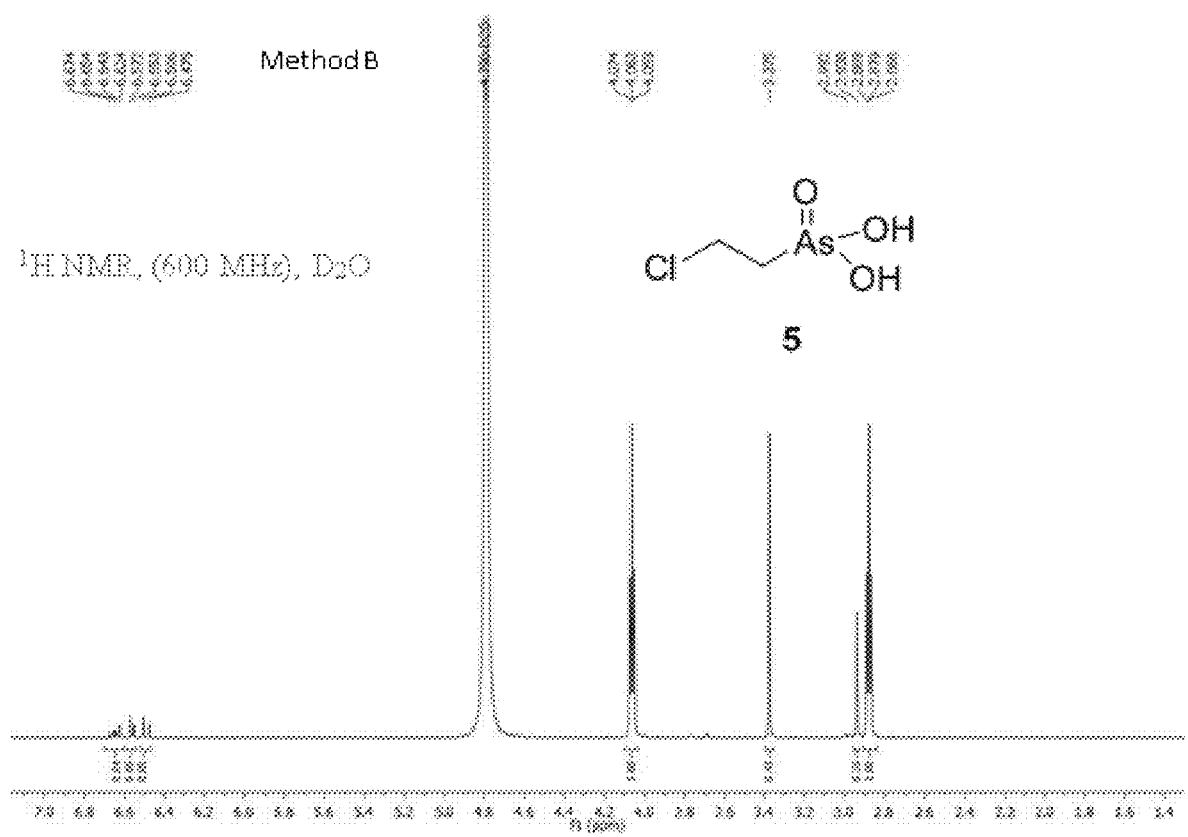

(t, J=11.6 Hz, 0.1H), 6.65 (dd, J=18.4, 11.6 Hz, 0.1H) (FIG. 7C); HRMS calcd for $C_2H_6AsO_4$ [M-H]$^-$ 186.9149, found 186.9151.

Figure 8:
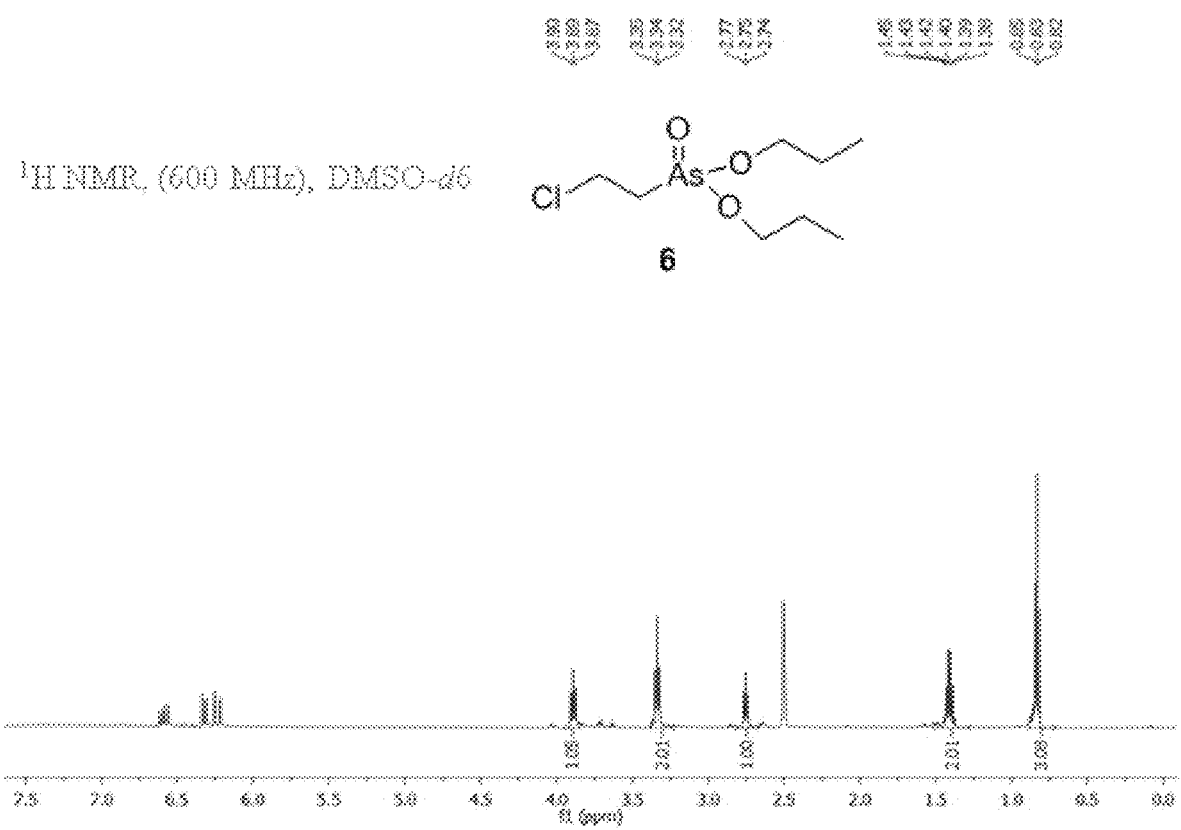
FIG. 8 shows the NMR data of compound 6.

2-Amino-4-arsonobutanoic acid (AST-OH, 8). Via esterification of S. (Step a): 1-Propanol (25 mL) was added into a round bottom flask containing 5 (5 g, 26.5 mmol; from Method A), and the resulting mixture was refluxed in an oil bath at 115° C. for 48 h. Volatiles were evaporated under reduced pressure to give dipropyl (2-chloroethyl)arsonate 6 (5.3 g, 73%) as a gummy solid containing ~30% of dipropyl vinylarsonate, as judged by the NMR signals for the vinylic protons at 6.15-6.72 ppm: $^1H$ NMR (DMSO-$d_6$) δ 0.83 (t, J=7.2 Hz, 6H), 1.41 (sext, J=7.4 Hz, 4H), 2.76 (t, J=7.5 Hz, 2H), 3.34 (t, J=7.0 Hz, 4H), 3.89 (t, J=7.5 Hz, 2H) (FIG. 8).

(Step b) Sodium (170 mg, 7.4 mmol) was added into a dry flask containing 3 mL of anhydrous EtOH and the mixture was stirred at ambient temperature until the sodium dissolved. Then diethylacetamidomalonate (1.2 g, 5.5 mmol) was added, and the resulting mixture was stirred for 5 min, followed by addition of a freshly prepared solution of 6 containing ~30% of dipropyl vinylarsonate (500 mg, 1.84 mmol dissolved in 2 mL EtOH). The resulting mixture was stirred at 70° C. in an oil bath for 4 h. Volatiles were evaporated under reduced pressure, yielding crude diethyl 2-acetamido-2-(2-dipropoxyarsoryl)ethyl)malonate (7a) or 7b as a brownish solid (~2 g), which was directly used in next step.

Figure 9A:
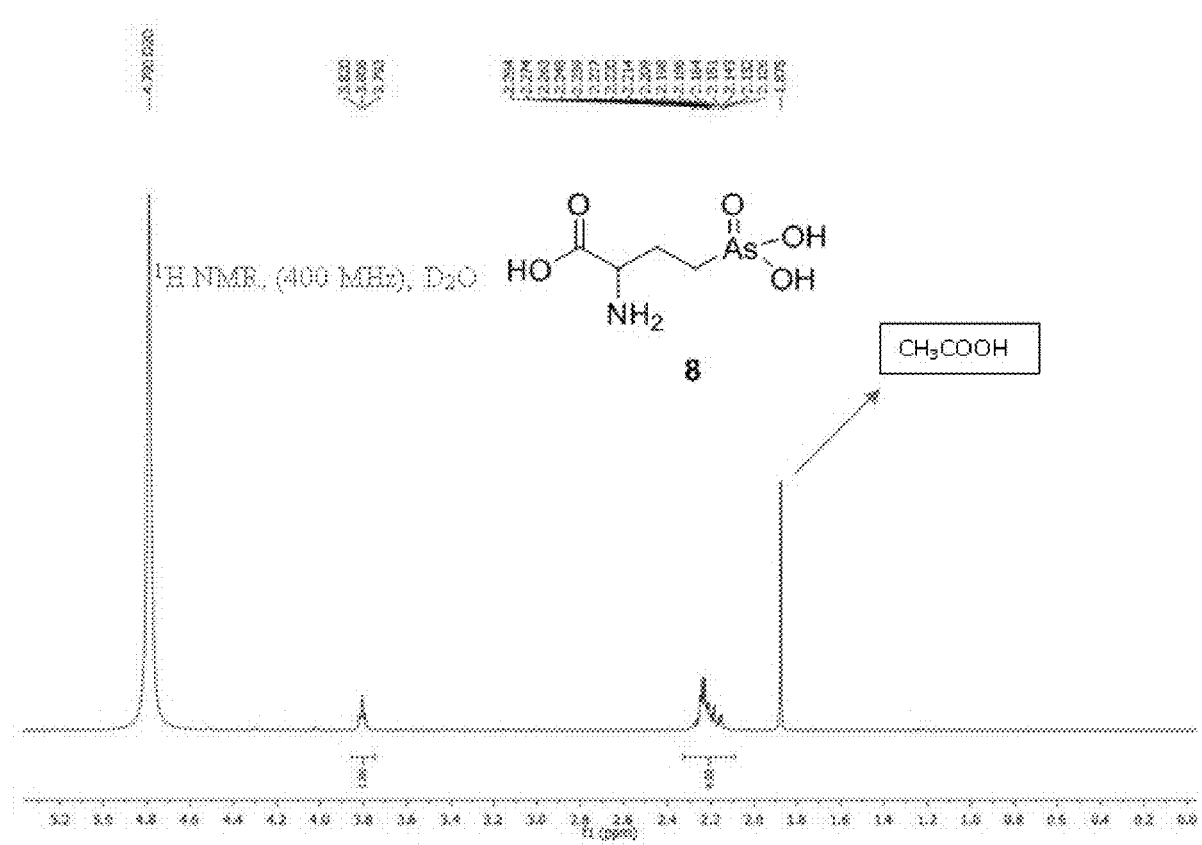
FIGS. 9A-9B show the NMR data of compound 8.
Figure 9B:
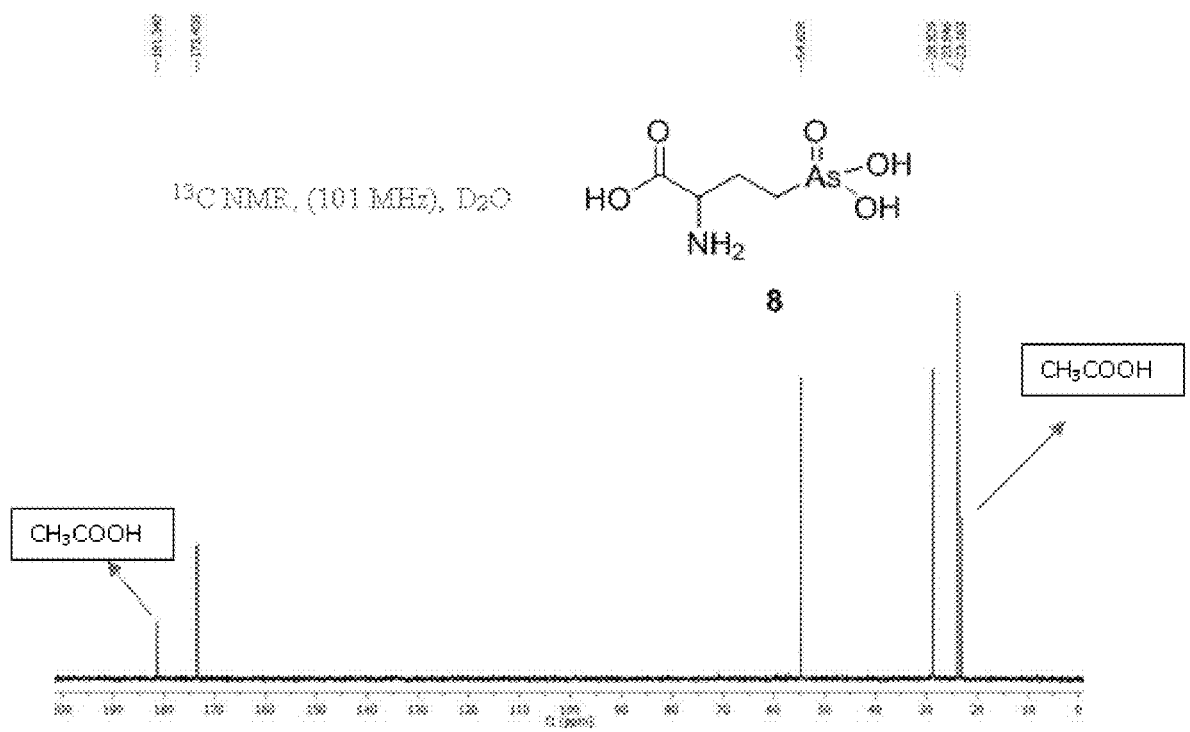

(Step c) 6 M HCl (6 mL) was added into the crude 7a or 7b, and the resulting mixture was refluxed at 120° C. in an oil bath for 3 h. Volatiles were evaporated, and the residue was dissolved in 20 mL $H_2O$. The solution was applied to a Dowex® 50WX8 (H$^+$ form) column (30×1 cm, 10 g), which was washed with 50 mL of $H_2O$. The product was eluted with a solution of $NH_4OH$ (0.5 M, 100 mL). Fractions from the ammonium elution (~100 mL) were evaporated under reduced pressure, and the residue was dissolved in 40 mL $H_2O$. The diluted solution was passed through a (Dowex® 50WX8 H$^+$ form) column (30×1 cm, 12 g) equilibrated with a weakly acidic triethylammonium acetate (TEAA) buffer solution (acetic acid 30 mM and triethylamine 15 mM). Compound 8 (TLC, $R_f$ 0.35, i-PrOH/$H_2O$/$NH_4OH$, 5:2:3; identified by staining with 1% ninhydrin solution) eluted with the same buffer followed by glycine byproduct (TLC, $R_f$ 0.55). The appropriate fractions were evaporated and co-evaporated (3×) with a mixture of EtOH/$H_2O$ (1:1, 12 mL) to afford 8 (100 mg, 24% from 6) as a white solid: $^1H$ NMR ($D_2O$) δ 2.13-2.28 (m, 4H), 3.81 (t, J=5.2 Hz, 1H) (FIG. 9A); $^{13}C$ NMR ($D_2O$) δ 23.85, 28.83, 54.63, 173.41 (FIG. 9B); HRMS calcd for $C_4H_9AsNO_5$ [M-H]$^-$ 225.9702, found 225.9703.

Figure 10:
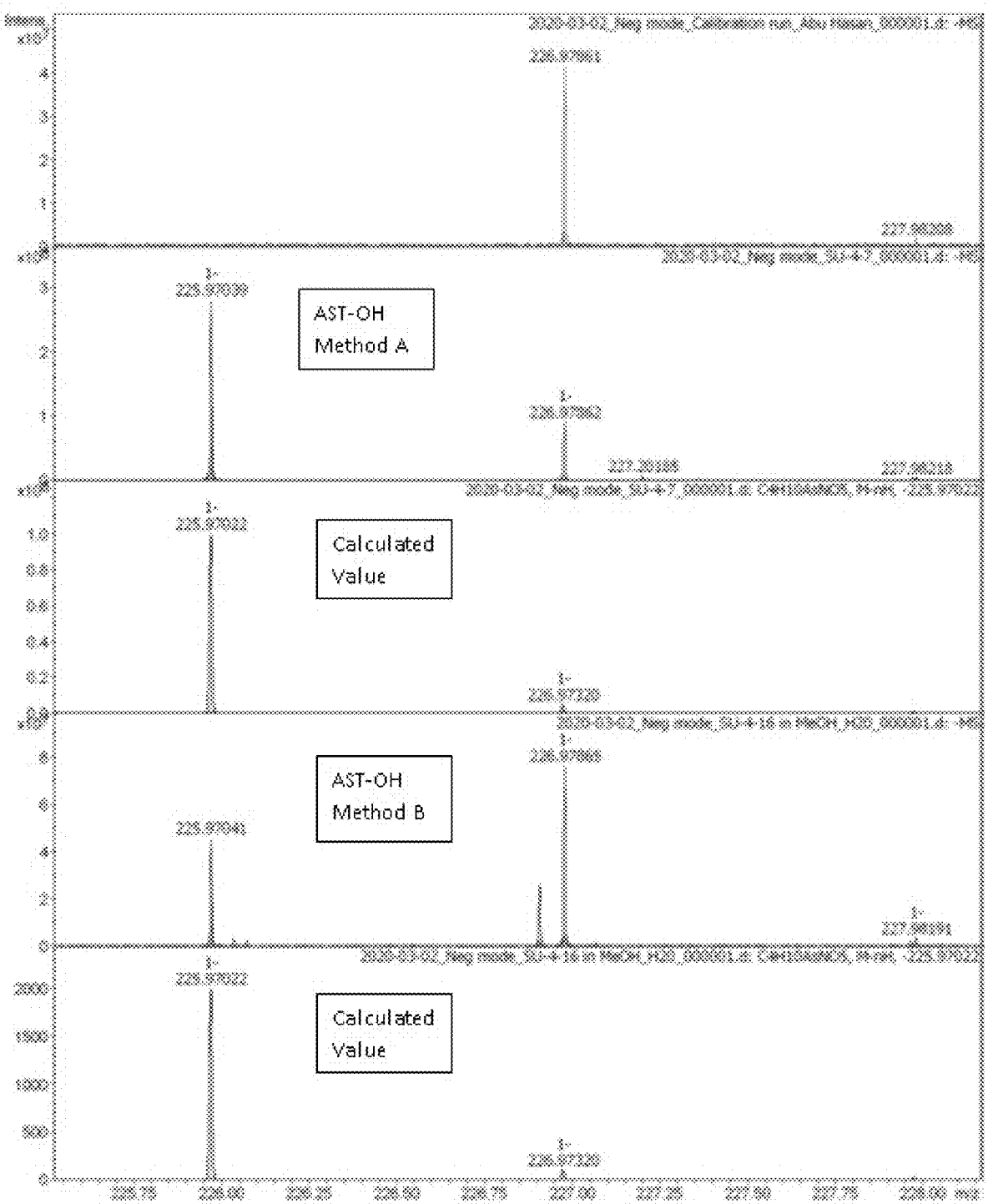
FIG. 10 shows the HRMS data of AST-OH.

Via Direct Condensation of 5. Treatment of 5 (500 mg, 5.65 mmol; from Method A) with sodium (244 mg, 10.6 mmol) and diethylacetamidomalonate (1.74 g, 8.0 mmol) in 10 mL anhydrous EtOH as described above in steps b and c gave 8 (337 mg, 56% from 5): HRMS [M-H]$^-$ found 225.9704 (FIG. 10, Method A).

Subjection of 5 (800 mg, 4.25 mmol; from Method B) to the same protocol as described above (steps b and c) also gave 8 (95 mg, 10% from 5): HRMS [M-H]$^-$ found 225.9704 (FIG. 10, Method B).

Enzymatic Methylation of AST-OH to Form AST

AST-OH was methylated by the enzyme CmArsM. CmArsM was expressed and purified as described previously. Briefly, cells of E. coli BL21 (DE3) pET28-arsM7B were grown at 37° C. in LB medium supplemented with 25 μg/ml kanamycin to an absorbance of 0.5 at 600 nm, at which time 0.3 mM isopropyl β-d-1-thiogalactopyranoside was added to induce expression of CmArsM. The cells were grown for another 4 h, harvested by centrifugation (5,000×g) at 4° C. for 20 min, washed once with Buffer A (50 mM morpholinopropane-1-sulfonic acid (MOPS), pH 7.5, containing 20% (wt/vol) glycerol, 0.5 M NaCl, 20 mM imidazole, and 10 mM 2-mercaptoethanol), and suspended in 5 ml of Buffer A per g of wet cells. The cells were lysed by a single pass through a French pressure cell at 20,000 psi, and 2.5 μL per g wet cell of the protease inhibitor diisopropyl fluorophosphate was added immediately. Membranes and unbroken cells were removed by centrifugation at 150,000×g for 1 h, and the supernatant solution was loaded at a flow rate of 0.5 ml/min onto a Ni(II)-NTA column preequilibrated with Buffer A. The column was then washed with 150 ml of Buffer A, followed by elution with 60 ml of Buffer A with a concentration gradient of imidazole from 0 to 0.2 M. CmArsM was identified by sodium dodecyl sulfate polyacrylamide gel electrophoresis (SDS-PAGE). Fractions containing CmArsM were concentrated by centrifugation using a 10-kDa-cutoff Amicon Ultrafilter (MilliporeSigma, Burlington, Mass.). Protein concentrations were estimated by the method of Bradford using BSA (MilliporeSigma) as a standard. Chemically synthesized AST-OH was reduced to trivalent As(III)T-OH as described previously. Briefly, 0.4 mM AST-OH (8, Method A) was reduced to As(III)T-OH with a mixture of 27 mM $Na_2S_2O_3$, 66 mM $Na_2S_2O_5$, and 82 mM $H_2SO_4$, followed by adjustment of the pH to 6 with NaOH. 10 μM As(III)T-OH was methylated by incubation with 0.5 mM S-adenosylmethionine and 4 μM CmArsM in a buffer consisting of 0.1 M MOPS, 0.15 M KCl and 1 mM tris(2-carboxyethyl)phosphine (TCEP), pH 7.0, at 37° C. overnight. The reaction solution was filtered using an Amicon Ultra Centrifugal Filter with a 3K cutoff membrane (MilliporeSigma) to remove protein.

Arsenic Speciation by HPLC-ICP-MS

Figure 11:
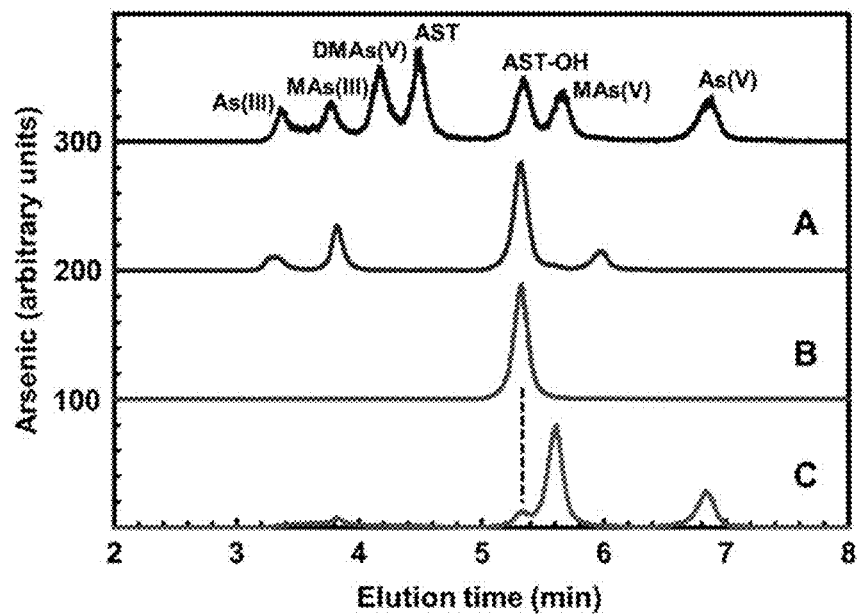
FIG. 11 shows HPLC-ICP-MS analysis of chemically synthesized AST-OH. Line A, crude AST-OH synthesized by Method A; Line B, purified AST-OH from Method A; Line C, crude AST-OH synthesized by Method B. Abbreviations: As(III), arsenite; MAs(III), methylarsenite; DMAs(V), dimethylarsenate; AST, arsinothricin; AST-OH, hydroxyarsinothricin; MAs(V), methylarse-nate; As(V), arsenate.
Figure 14:
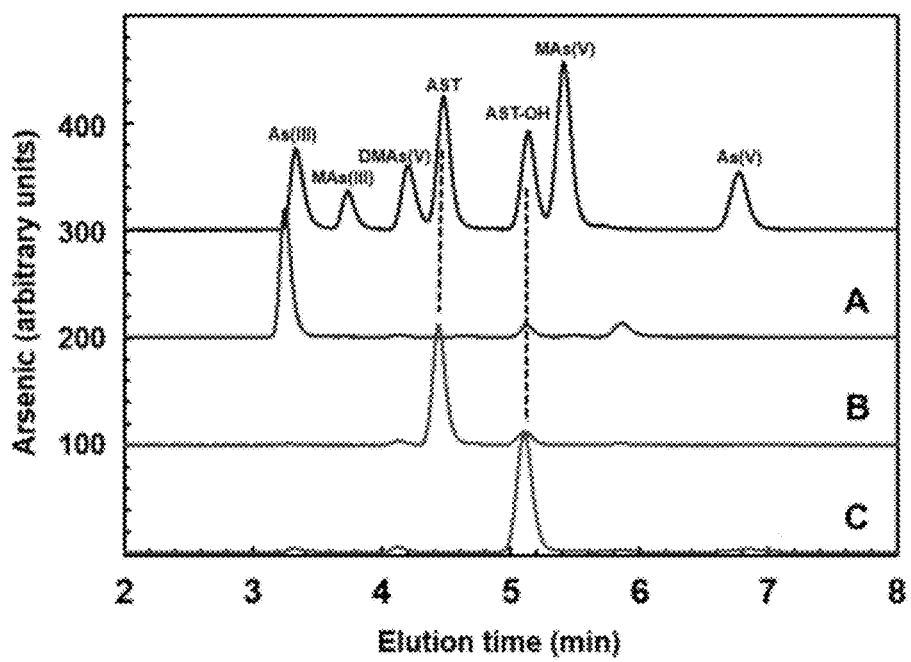
FIG. 14 shows enzymatic methylation of AST-OH to produce AST. Reduced As(III)T-OH (line A) was incubated in the presence (line B) or absence (line C) of CmArsM, and the arsenic species in the reaction solutions were analyzed by HPLC-ICP-MS. Reaction conditions: Reduction step, 0.4 mM AST-OH was mixed with 27 mM $Na_2S_2O_3$, 66 mM $Na_2S_2O_5$, and 82 mM $H_2SO_4$, followed by pH adjusted to 6 with NaOH; Methylation and oxidation steps, 10 μM of As(III)T-OH was incubated with 0.5 mM SAM and 4 μM ArsM at 37° C. overnight.

Arsenic species, including trivalent and pentavalent forms of AST-OH and AST were analyzed by high pressure liquid chromatography (HPLC) (Series 2000; PerkinElmer, Waltham, Mass.) coupled to inductively coupled plasma mass spectrometry (ICP-MS) (ELAN DRC-e; PerkinElmer), as described previously, with minor modifications. Briefly, arsenic species in samples were separated by HPLC on a BioBasic™ 18 LC column (250 mm×4.6 mm, 5 μm, 300 Å) (Thermo Fisher Scientific, Waltham, Mass.) using a mobile phase consisting of 3 mM malonic acid and 5% methanol (v/v) (pH 5.6 adjusted with tetrabutylammonium hydroxide) with a flow rate of 1 mL min$^{-1}$ at 25° C. Arsenic was monitored by ICP-MS. Arsenic species were determined from the HPLC retention time of known standards (FIGS. 11 and 14).

Example 1—Synthesis of AST-OH by Method A

Figure 3:
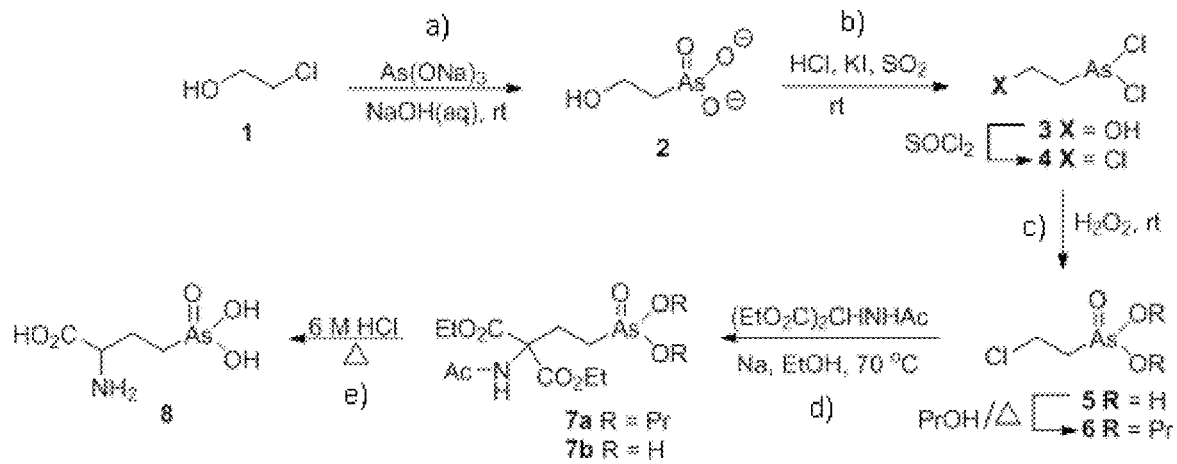
FIG. 3 shows the synthesis scheme of AST-OH by method A.

AST-OH 8 was prepared from arsonic acid 2 by modification of the reported method in Scheme 1 (FIG. 3). Treatment of 2-chloroethanol 1 (0.62 mol) with $Na_3AsO_3$ generated in situ from arsenic trioxide (0.5 equiv) and aqueous NaOH (3 equiv), afforded crude (2-hydroxyethyl)arsonic acid 2 with unidentified impurities (based on $^1H$ NMR) (FIG. 4A). Arsenite acts as a nucleophile that displaces the chlorine atom to give pentavalent arsonic acid 2. To substitute the ethylene hydroxyl group in 2 with a chloride atom to get 5, polar pentavalent arsonic acid 2 was reduced to the less polar trivalent arsine derivative 3. Treatment of crude 2 with $SO_2$ gas (3 equiv) in the presence of catalytic amounts of KI and excess HCl afforded dichloro-(2-hydroxyethyl) arsine 3. An excess of hydrochloric acid was required to minimize hydrolysis of 3. Subsequent reaction of crude 3 with thionyl chloride (2.5 equiv) yielded pure dichloro-(2-chloroethyl)arsine 4 in a 52% yield (overall from 1) after vacuum distillation. The arsine 4 was oxidized into (2-chloroethyl)arsonic acid 5 with excess $H_2O_2$. To prevent decomposition of 5, the reaction mixture was carefully evaporated under reduced pressure, providing pure 5 (65%) after recrystallization from acetone/ethyl ether. The structure of 5 was confirmed from HRMS and NMR data (FIG. 7).

Reflux of 5 with anhydrous propanol afforded the propyl ester 6 (73%), which contained ~30% of the vinyl arsonic byproduct(s) formed by elimination of HCl. Treatment of crude 6 with diethyl acetamidomalonate (3 equiv) in the presence of freshly prepared sodium ethoxide (4 equiv) at 70° C. yielded the crude malonate product 7a. Heating the reaction mixture is necessary since this reaction at ambient temperature failed to produce 7a. Reflux of crude 7a in 6 M HCl effected global deprotection and decarboxylation to yield crude 8. Purification by cation exchange chromatography on a Dowex® 50WX8 ($H^+$ form) column with triethylammonium acetate (TEAA)/AcOH buffer afforded 2-amino-4-arsonobutanoic acid 8 (18%, from 5). Esterification of (2-chloroethyl)arsonic 5 was found not to be necessary since subjection of 5 directly to coupling with diethyl acetamidomalonate followed by deprotection and decarboxylation also provided AST-OH 8 (56%). HPLC-ICP-MS analysis suggests that the purity of the crude 8 and the purified 8 is approximately 60% and nearly 100%, respectively, with respect to arsenic (FIG. 11, lines A and B).

Example 2—Synthesis of AST-OH by Method B

Figure 12:
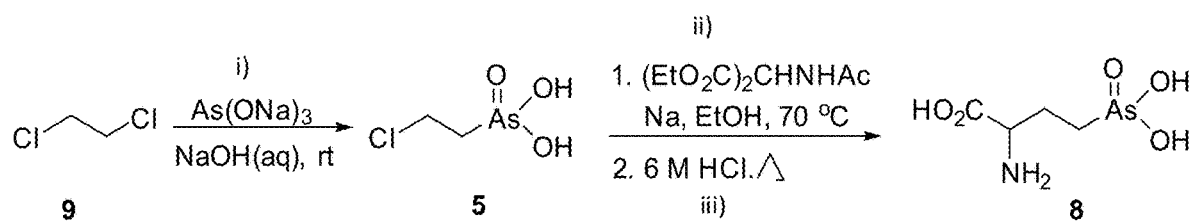
FIG. 12 shows the synthesis scheme of AST-OH by method B.

A shorter 3-steps synthesis of AST-OH from 1,2-dichloroethane was also developed (FIG. 12). Condensation of 1,2-dichloroethane 9 with basic sodium arsenite afforded (2-chloroethyl)arsonic acid 5 (13%) in a single step. Product 5 contained ~10% of vinyl arsonic byproduct(s) as judged by the appearance of the characteristic vinylic peaks from $CH_2{=}CH$ group in the $^1H$ NMR spectrum in addition to the 1,2-diarsonoethane adduct detected in HRMS. This approach eliminates (a) the necessity of conversion of the pentavalent (2-hydroxyethyl)arsonic acid to trivalent dichloro(2-hydroxyethyl)arsine with toxic $SO_2$ gas and (b) challenging displacement of hydroxyl group with chloride. Coupling of crude 5 with diethyl acetamidomalonate followed by deprotection and decarboxylation also yielded AST-OH 8 but in lower yield (10%). HPLC-ICP-MS analysis suggests that the purity is roughly 8% with respect to arsenic (FIG. 11, line C).

Example 3—Enzymatic Methylation of AST-OH to AST

When exposed to trivalent inorganic arsenite, *B. gladioli* GSRB05 initially produces AST-OH, followed by gradual biotransformation to AST, indicating that the final step of AST biosynthesis is methylation of AST-OH to AST. Microbial methylation of trivalent arsenicals is catalyzed by the enzyme ArsM, an As(III)S-adenosylmethionine (SAM) methyltransferase. AST-OH is structurally similar to methylarsenate (MAs(V)), which suggested that it could be a substrate for enzymatic methylation by ArsM to produce AST.

To examine this possibility, AST-OH was first chemically reduced to trivalent AST-OH (As(III)T-OH) with an acidic mixture of $Na_2S_2O_3$, $Na_2S_2O_5$ and $H_2SO_4$, and pH-neutralized with NaOH (FIG. 14, line A), and then incubated with purified CmArsM enzyme from *Cyanidioschyzon* sp. 5508 (FIG. 13). CmArsM catalyzed transfer of the S-methyl group of SAM to As(III)T-OH, nearly complete converting it into the trivalent form of AST (As(III)T), presumably as a mixture of the D/L-enantiomers, which then spontaneously oxidized in air to the final product, AST (FIG. 14, line B). In the absence of CmArsM, most of the As(III)T-OH reoxidized to AST-OH (FIG. 14, line C). Thus, AST can be quantitatively produced from chemically synthesized AST-OH by enzymatic methylation.

All patents, patent applications, provisional applications, and publications referred to or cited herein are incorporated by reference in their entirety, including all figures and tables, to the extent they are not inconsistent with the explicit teachings of this specification.

It should be understood that the examples and embodiments described herein are for illustrative purposes only and that various modifications or changes in light thereof will be suggested to persons skilled in the art and are to be included within the spirit and purview of this application and the scope of the appended claims. These examples should not be construed as limiting. In addition, any elements or limitations of any invention or embodiment thereof disclosed herein can be combined with any and/or all other elements or limitations (individually or in any combination) or any other invention or embodiment thereof disclosed herein, and all such combinations are contemplated within the scope of the invention without limitation thereto.

We claim:

1. A derivative of arsinothricin (AST) having a general structure of formula (I)

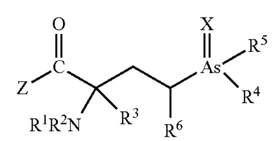

or (I')

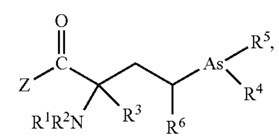

wherein X is O or S;

Z is $OR^7$, $NHR^8$, $NR^8R^9$ or $NHCHR^{20}R^{11}$;

$R^1$ and $R^2$ are independently selected from hydrogen, alkyl, substituted alkyl, aryl, substituted aryl, cycloalkyl, substituted cycloalkyl, acyl, benzyl, and benzoyl;

$R^3$ is hydrogen, alky, substituted alkyl, cycloalkyl, substituted cycloalkyl, alkoxy or hydroxylalkyl;

$R^4$ is OH, $OR^{14}$, alkyl, substituted alkyl, aryl, substituted aryl, heteroalkyl, substituted heteroalkyl, cycloalkyl, substituted cycloalkyl, acyl, benzyl, benzoyl or sulfhydryl;

$R^5$ is alkyl, substituted alkyl, aryl, substituted aryl, heteroalkyl, substituted heteroalkyl, cycloalkyl, substituted cycloalkyl, acyl, benzyl, benzoyl or sulfhydryl;

$R^6$ is hydrogen, halogen, alkyl, substituted alkyl, acyl, alkoxy, cycloalkyl, substituted cycloalkyl, amino, substituted amino, or hydroxyl;

$R^7$ is hydrogen, alkyl, substituted alkyl, aryl, substituted aryl, benzyl, benzoyl, cycloalkyl, substituted cycloalkyl, heteroalkyl, or substituted heteroalkyl;

$R^8$ is hydrogen, alkyl, substituted alkyl, substituted alkyl, aryl, substituted aryl, cycloalkyl, substituted cycloalkyl, heteroalkyl, substituted heteroalkyl, acyl, alkoxy, benzyl, and benzoyl;

$R^9$ is hydrogen, alkyl, substituted alkyl, aryl, substituted aryl, cycloalkyl, substituted cycloalkyl, heteroalkyl, substituted heteroalkyl, acyl, alkoxy, benzyl, or benzoyl;

$R^{10}$ is hydrogen, alkyl, substituted alkyl, substituted alkyl, aryl, substituted aryl, cycloalkyl, substituted cycloalkyl, heteroalkyl, substituted heteroalkyl, acyl, alkoxy, amino, or substituted amino, benzyl, and benzoyl;

$R^{11}$ is hydrogen, alkyl, substituted alkyl, aryl, substituted aryl, cycloalkyl, substituted cycloalkyl, heteroalkyl, substituted heteroalkyl, acyl, alkoxy, benzyl, benzoyl amino, or substituted amino; and $R^{14}$ is alkyl, substituted alkyl, aryl, or substituted aryl, or a salt thereof.

2. The derivative of AST according to claim 1, the derivative having a structure of

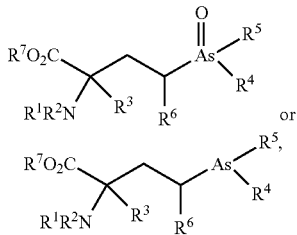

wherein $R^1$ and $R^2$ are independently selected from hydrogen, alkyl, substituted alkyl, aryl, substituted aryl, acyl, benzyl, and benzoyl;

$R^3$ is hydrogen, alky, substituted alkyl, alkoxy or hydroxylalkyl;

$R^4$ is OH, alkyl, substituted alkyl, aryl, substituted aryl, heteroalkyl, substituted heteroalkyl, acyl, benzyl, benzoyl or sulfhydryl;

$R^5$ is alkyl, substituted alkyl, aryl, substituted aryl, heteroalkyl, substituted heteroalkyl, acyl, benzyl, benzoyl or sulfhydryl;

$R^6$ is hydrogen, halogen, alkyl, substituted alkyl, acyl, alkoxy, amino, substituted amino, or hydroxyl; and $R^7$ is hydrogen, alkyl, substituted alkyl, aryl, substituted aryl, benzyl, benzoyl, heteroalkyl, or substituted heteroalkyl.

3. The derivative of AST according to claim 1, the derivative having a structure of

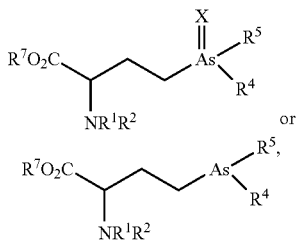

wherein $R^1$ and $R^2$ are independently selected from hydrogen, alkyl, substituted alkyl, aryl, substituted aryl, acyl, benzyl, and benzoyl;

$R^4$ is OH, alkyl, substituted alkyl, aryl, substituted aryl, heteroalkyl, substituted heteroalkyl, acetyl, benzyl, benzoyl or sulfhydryl;

$R^5$ is alkyl, substituted alkyl, aryl, substituted aryl, heteroalkyl, substituted heteroalkyl, acyl, benzyl, benzoyl or sulfhydryl; and $R^7$ is hydrogen, alkyl, substituted alkyl, aryl, substituted aryl, benzyl, benzoyl, heteroalkyl, or substituted heteroalkyl.

4. The derivative of AST according to claim 1, the derivative having a structure of

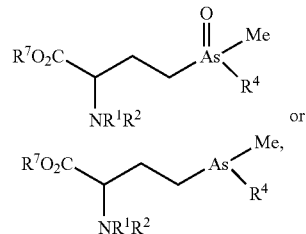

wherein $R^1$ and $R^2$ are independently selected from hydrogen, alkyl, substituted alkyl, aryl, substituted aryl, acyl, benzyl, and benzoyl;

$R^4$ is OH, alkyl, substituted alkyl, aryl, substituted aryl, heteroalkyl, substituted heteroalkyl, acetyl, benzyl, benzoyl or sulfhydryl; and $R^7$ is hydrogen, alkyl, substituted alkyl, aryl, substituted aryl, benzyl, benzoyl, heteroalkyl, or substituted heteroalkyl.

5. The derivative of AST according to claim 1, the derivative having a structure of

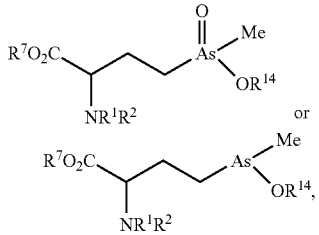

wherein $R^1$ and $R^2$ are independently selected from hydrogen, alkyl, substituted alkyl, aryl, substituted aryl, acyl, benzyl, and benzoyl;

$R^7$ is hydrogen, alkyl, substituted alkyl, aryl, substituted aryl, benzyl, benzoyl, heteroalkyl, or substituted heteroalkyl; and $R^{14}$ is alkyl, substituted alkyl, aryl, or substituted aryl.

6. The derivative of AST according to claim 1, the derivative having a structure of

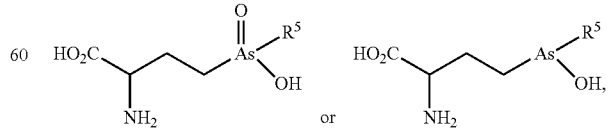

wherein $R^5$ is alkyl, $CH_2NH_2$ or OH.

7. The derivative of AST according to claim 1, the derivative having a structure of:

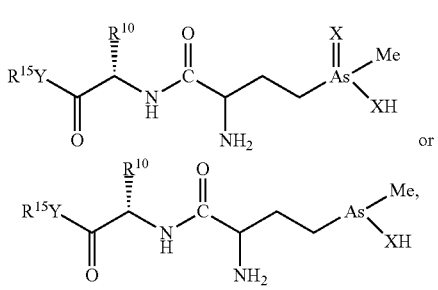

wherein X is O or S; Y is N or O; $R^{10}$ is hydrogen, alkyl, substituted alkyl, aryl, substituted aryl, cycloalkyl, substituted cycloalkyl, heteroalkyl, substituted heteroalkyl, acyl, alkoxy, amino, substituted amino, benzyl, or benzoyl; and $R^{15}$ is hydrogen, alkyl, substituted alkyl, aryl, substituted aryl, cycloalkyl, substituted cycloalkyl, heteroalkyl, substituted heteroalkyl, acyl, alkoxy, benzyl, or benzoyl.

8. The derivative of AST according to claim 7, wherein Y is N; and $R^{15}Y$ is Ala, Leu, Val, Ala-Ala, Ala-Leu, or Ala-Ala-Ala.

9. The derivative of AST according to claim 7, wherein Y is N; and $R^{15}Y$ is a peptide comprising n amino acids, wherein $2 \leq n \leq 10$.

10. The derivative of AST according to claim 1, wherein Z is $NHR^8$, or $NR^8R^9$.

11. The derivative of AST according to claim 1, wherein X is O or S;
Z is $NHR^8$, or $NR^8R^9$;
$R^1$ and $R^2$ are independently selected from hydrogen, alkyl, substituted alkyl, aryl, substituted aryl, acetyl, benzyl, and benzoyl;
$R^3$ is hydrogen or alkyl;
$R^4$ is OH, alkyl, substituted alkyl, aryl, substituted aryl, heteroalkyl, substituted heteroalkyl, acetyl, benzyl, benzoyl or sulfhydryl;
$R^5$ is alkyl, substituted alkyl, aryl, substituted aryl, heteroalkyl, substituted heteroalkyl, acetyl, benzyl, benzoyl or sulfhydryl;
$R^6$ is hydrogen, or hydroxyl;
$R^8$ is alkyl, substituted alkyl, substituted alkyl, aryl, substituted aryl, cycloalkyl, substituted cycloalkyl, acyl, or alkoxy; and
$R^9$ is hydrogen, alkyl, substituted alkyl, aryl, substituted aryl, cycloalkyl, substituted cycloalkyl, acyl, or alkoxy.

12. The derivative of AST according to claim 1, wherein Z is $NHR^8$, or $NR^8R^9$; $R^1$ and $R^2$ are independently selected from methyl, acetyl, $CF_3CO$, benzoyl and benzyl; $R^3$ is hydrogen or alkyl; $R^4$ is OH, $OR^{14}$, alkyl, substituted alkyl, acetyl, benzyl, benzoyl or sulfhydryl; $R^5$ is alkyl, substituted alkyl; $R^6$ is hydrogen, or hydroxyl; and $R^{14}$ is H, methyl, ethyl, propyl, phenyl, or acetoxymethyl.

13. The derivative of AST according to claim 12, wherein $R^4$ is methyl, phenyl, sulfhydryl or thiomethyl.

14. The derivative of AST according to claim 11, $R^8$ is methyl, ethyl, propyl, isopropyl, acetoxymethyl, phenyl, $CH_2Ph$ or benzyl; and $R^9$ is hydrogen, methyl, ethyl, propyl, isopropyl, acetoxymethyl, phenyl, $CH_2Ph$ or benzyl.

15. A pharmaceutical composition comprising a derivative of AST according to claim 1, or a salt thereof, and a pharmaceutically acceptable carrier.

16. A method of treating an infection in a subject caused by *Mycobacterium tuberculosis*, *Mycobacterium Bovis*, or *Enterobacter cloacae* comprising administering to the subject the pharmaceutical composition of claim 15.

17. The method of claim 16, the infection being caused by *Mycobacterium tuberculosis* or *Mycobacterium brevis*.

18. The method of claim 16, the infection being caused by carbapenem-resistant *Enterobacter cloacae*.

19. The method of claim 16, the administration being via oral, pulmonary, buccal, suppository, intravenous, intraperitoneal, intranasal, intramuscular, or subcutaneous route.

20. The method of claim 16, the pharmaceutical composition comprising a derivative of AST selected from

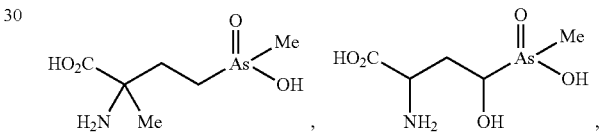

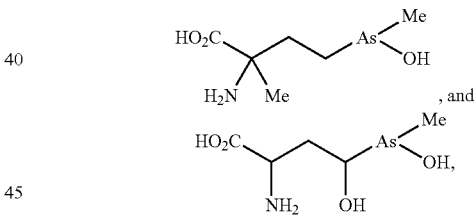

or a salt thereof.

* * * * *